(12) United States Patent
Kurokawa et al.

(10) Patent No.: US 8,148,111 B2
(45) Date of Patent: Apr. 3, 2012

(54) CELL CULTURE CARRIER COMPRISING POLY(METH)ACRYLIC (SALT) PARTICLE AND ARTIFICIAL POLYPEPTIDE

(75) Inventors: Masato Kurokawa, Kyoto (JP); Kazuhiro Takahashi, Kyoto (JP)

(73) Assignee: Sanyo Chemical Industries, Ltd., Kyoto-shi (JP)

( * ) Notice: Subject to any disclaimer, the term of this patent is extended or adjusted under 35 U.S.C. 154(b) by 826 days.

(21) Appl. No.: 12/293,147

(22) PCT Filed: Mar. 13, 2007

(86) PCT No.: PCT/JP2007/000217
§ 371 (c)(1),
(2), (4) Date: Sep. 16, 2008

(87) PCT Pub. No.: WO2007/108205
PCT Pub. Date: Sep. 27, 2007

(65) Prior Publication Data
US 2009/0136912 A1    May 28, 2009

(30) Foreign Application Priority Data
Mar. 17, 2006 (JP) ................. 2006-074009

(51) Int. Cl.
C12P 21/00 (2006.01)
C12N 11/08 (2006.01)
C12N 5/00 (2006.01)
C12N 5/07 (2010.01)

(52) U.S. Cl. ............ 435/70.1; 435/70.3; 435/71.1; 435/180; 435/383; 435/396; 435/403

(58) Field of Classification Search .................. None
See application file for complete search history.

(56) References Cited

U.S. PATENT DOCUMENTS

| | | | |
|---|---|---|---|
| 4,066,584 A | | 1/1978 | Allen et al. |
| 5,244,799 A | | 9/1993 | Anderson |
| 5,330,911 A | * | 7/1994 | Hubbell et al. ............ 435/402 |
| 5,562,099 A | * | 10/1996 | Cohen et al. ............ 600/458 |
| 5,998,553 A | * | 12/1999 | Iida et al. ............ 526/193 |
| 6,884,628 B2 | * | 4/2005 | Hubbell et al. ............ 436/518 |
| 7,576,051 B2 | * | 8/2009 | Kurokawa et al. ............ 514/1.1 |
| 2006/0252152 A1 | * | 11/2006 | Alstine et al. ............ 435/404 |

FOREIGN PATENT DOCUMENTS

| | | |
|---|---|---|
| JP | 3-502935 A | 7/1991 |
| JP | 4-135481 A | 5/1992 |
| JP | 11-5808 A | 1/1999 |
| JP | 2001-2935 A | 1/2001 |
| JP | 2002-191353 A | 7/2002 |
| JP | 2003-165883 A | 6/2003 |
| JP | 2003-169669 A | 6/2003 |
| JP | 2003-189848 A | 7/2003 |
| JP | 2009-072081 A | 4/2009 |

OTHER PUBLICATIONS

"Microcarrier cell culture principles & methods"; Pharmacia Biotech, pp. 27-31, Oct. 10, 1996, pp. 26-31.
K. Shivakumar et al.; "Cell adhesion and growth on synthetic hydrogel beads"; Bull. Mater. Sci., vol. 12, No. 1, pp. 27-32, Mar. 1989.
A. Jayakrishnan et al.; "Hydrogel microspheres from crosslinked poly (methyl methacrylate): synthesis and biocompatibility studies"; Bull. Mater. Sci., vol. 12, No. 1, pp. 17-25, 1989.
A. Esty; "Receptor-specific serum-free cell attachment using a highly stable engineered protein polymer"; American Biotechnology Laboratory, vol. 9, No. 3, p. 44. 1991.
J. Capello et al.; "The design and production of bioactive protein polymers for biomedical applications"; Polymer Preprints, vol. 31, No. 1, pp. 193-194. 1994.
International Search Report of PCT/JP2007/00217, date of mailing Jun. 19, 2007.
Japanese Office Action dated Jun. 29, 2010, issued in corresponding Japanese Patent Application No. 2007-063893.
Notification of Transmittal of Translation of the International Preliminary Report on Patentability (Form PCT/IB/338) of International Application No. PCT/JP2007/000217 mailed Oct. 30, 2008 with Forms PCT/IB/373 and PCT/ISA/237.
Rosso, F. et al.; "New polyelectrolyte hydrogels for biomedical applications"; Materials Science and Engineering: C, [Online] vol. 23, No. 3, Mar. 3, 2003, pp. 371-376; XP002621052.
Hutcheon, G. A. et al.; "Water absorption and surface properties of novel poly(ethylmethacrylate) polymer systems for use in bone and cartilage repair"; Biomaterials, vol. 22, No. 7, Apr. 2001, pp. 667-676, XP002621053.
Fussell, Garland W. et al.; "Synthesis and characterization of acrylic terpolymers with RGD peptides for biomedical applications"; Biomaterials, Elsevier Science Publishers BV., Barking, GB, vol. 25, No. 15, Jul. 1, 2004, pp. 2971-2978, XP004489048.
Jacob, Jean T et al..; "Corneal epithelial cell growth over tethered-protein/peptide surface-modified hydrogels" Journal of Biomedical Materials Research, vol. 72B, No. 1, Jan. 15, 2005, pp. 198-205, XP002621049.
Yang, Jen-Ming et al.; "Preparation of poly(acrylic acid) modified polyurethane membrane for biomaterial by UV radiation without degassing"; Journal of Biomedical Materials Research, vol. 45, No. 2, May 1999, pp. 133-139, XP002621051.

(Continued)

*Primary Examiner* — David Naff
(74) *Attorney, Agent, or Firm* — Westerman, Hattori, Daniels & Adrian, LLP

(57) ABSTRACT

A carrier for cell culture is provided which improves the cell proliferativity in serum-free culture and which is free from risk from infection factor contamination. The gist of the features of the present invention is to be formed of a crosslinked poly(meth)acrylic acid (salt) particle (A) and an artificial polypeptide (P) having at least one cell-adhesive minimal amino acid sequence (X) in one molecule and to have a water retention value of from 2 to 50 g/g. The (A) is preferably a particle produced by reversed phase suspension polymerization of an aqueous monomer solution containing (meth)acrylic acid and/or an alkali metal salt of (meth)acrylic acid. The (P) preferably has at least one auxiliary amino acid sequence (Y) in one molecule of the (P). The (X) is preferably an Arg Gly Asp sequence.

14 Claims, No Drawings

OTHER PUBLICATIONS

Bi, JingJing et al.; "Tethered Protein/Peptide-Surface-Modified Hydrogels"; Journal of Biomaterials Science Polymer Edition, VSP, Utrecht, NL, vol. 15, No. 7, Jan. 1, 2004, pp. 905-916, XP009076823.

Berg, Michael C. et al.; "Controlling Mammalian Cell Interactions on Patterned Polyelectrolyte Multilayer Surfaces"; Langmuir, The ACS Journal of Surfaces and Colloids, Feb. 17, 2004 LNKD-PUBMED: 15803720, vol. 20, No. 4, Feb. 17, 2004, pp. 1362-1368, XP002621050.

Supplementary European Search Report of European Application No. 07736876, Feb. 2011.

Chinese Office Action dated May 25, 2011, issued in corresponding Chinese Patent Application No. 200780009488.2.

* cited by examiner

SEQUENCE LISTING

<160> NUMBER OF SEQ ID NOS: 64

<210> SEQ ID NO 1
<211> LENGTH: 4
<212> TYPE: PRT
<213> ORGANISM: Homo sapiens

<400> SEQUENCE: 1

Arg Glu Asp Val

```
<210> SEQ ID NO 2
<211> LENGTH: 5
<212> TYPE: PRT
<213> ORGANISM: Homo sapiens

<400> SEQUENCE: 2

Tyr Ile Gly Ser Arg
1               5

<210> SEQ ID NO 3
<211> LENGTH: 5
<212> TYPE: PRT
<213> ORGANISM: Homo sapiens

<400> SEQUENCE: 3

Pro Asp Ser Gly Arg
1               5

<210> SEQ ID NO 4
<211> LENGTH: 7
<212> TYPE: PRT
<213> ORGANISM: Homo sapiens

<400> SEQUENCE: 4

Arg Tyr Val Val Leu Pro Arg
1               5

<210> SEQ ID NO 5
<211> LENGTH: 6
<212> TYPE: PRT
<213> ORGANISM: Homo sapiens

<400> SEQUENCE: 5

Leu Gly Thr Ile Pro Gly
1               5

<210> SEQ ID NO 6
<211> LENGTH: 10
<212> TYPE: PRT
<213> ORGANISM: Homo sapiens

<400> SEQUENCE: 6

Arg Asn Ile Ala Glu Ile Ile Lys Asp Ile
1               5                   10

<210> SEQ ID NO 7
<211> LENGTH: 5
<212> TYPE: PRT
<213> ORGANISM: Homo sapiens

<400> SEQUENCE: 7

Ile Lys Val Ala Val
1               5

<210> SEQ ID NO 8
<211> LENGTH: 4
<212> TYPE: PRT
<213> ORGANISM: Homo sapiens

<400> SEQUENCE: 8

Asp Gly Glu Ala
1
```

```
<210> SEQ ID NO 9
<211> LENGTH: 15
<212> TYPE: PRT
<213> ORGANISM: Homo sapiens

<400> SEQUENCE: 9

Gly Val Lys Gly Asp Lys Gly Asn Pro Gly Trp Pro Gly Ala Pro
1               5                   10                  15

<210> SEQ ID NO 10
<211> LENGTH: 13
<212> TYPE: PRT
<213> ORGANISM: Homo sapiens

<400> SEQUENCE: 10

Gly Glu Phe Tyr Phe Asp Leu Arg Leu Lys Gly Asp Lys
1               5                   10

<210> SEQ ID NO 11
<211> LENGTH: 8
<212> TYPE: PRT
<213> ORGANISM: Homo sapiens

<400> SEQUENCE: 11

Tyr Lys Leu Asn Val Asn Asp Ser
1               5

<210> SEQ ID NO 12
<211> LENGTH: 10
<212> TYPE: PRT
<213> ORGANISM: Mytilus edulis

<400> SEQUENCE: 12

Ala Lys Pro Ser Tyr Pro Pro Thr Tyr Lys
1               5                   10

<210> SEQ ID NO 13
<211> LENGTH: 12
<212> TYPE: PRT
<213> ORGANISM: Homo sapiens

<400> SEQUENCE: 13

Asn Arg Trp His Ser Ile Tyr Ile Thr Arg Phe Gly
1               5                   10

<210> SEQ ID NO 14
<211> LENGTH: 12
<212> TYPE: PRT
<213> ORGANISM: Homo sapiens

<400> SEQUENCE: 14

Thr Trp Tyr Lys Ile Ala Phe Gln Arg Asn Arg Lys
1               5                   10

<210> SEQ ID NO 15
<211> LENGTH: 12
<212> TYPE: PRT
<213> ORGANISM: Homo sapiens

<400> SEQUENCE: 15

Arg Lys Arg Leu Gln Val Gln Leu Ser Ile Arg Thr
1               5                   10

<210> SEQ ID NO 16
<211> LENGTH: 5
<212> TYPE: PRT
```

<213> ORGANISM: Homo sapiens

<400> SEQUENCE: 16

Pro His Ser Arg Asn
1               5

<210> SEQ ID NO 17
<211> LENGTH: 10
<212> TYPE: PRT
<213> ORGANISM: Artificial Sequence
<220> FEATURE:
<223> OTHER INFORMATION: auxiliary amino acid sequence

<400> SEQUENCE: 17

Gly Ala Gly Ala Gly Ala Gly Ala Gly Ala
1               5                   10

<210> SEQ ID NO 18
<211> LENGTH: 40
<212> TYPE: PRT
<213> ORGANISM: Artificial Sequence
<220> FEATURE:
<223> OTHER INFORMATION: auxiliary amino acid sequence

<400> SEQUENCE: 18

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala
        35                  40

<210> SEQ ID NO 19
<211> LENGTH: 160
<212> TYPE: PRT
<213> ORGANISM: Artificial Sequence
<220> FEATURE:
<223> OTHER INFORMATION: auxiliary amino acid sequence

<400> SEQUENCE: 19

Gly Ala Gly Ala Gly Ala Gly Ala Gly Ala Gly Ala Gly Ala Gly Ala
1               5                   10                  15

Gly Ala Gly Ala Gly Ala Gly Ala Gly Ala Gly Ala Gly Ala Gly Ala
            20                  25                  30

Gly Ala Gly Ala Gly Ala Gly Ala Gly Ala Gly Ala Gly Ala Gly Ala
        35                  40                  45

Gly Ala Gly Ala Gly Ala Gly Ala Gly Ala Gly Ala Gly Ala Gly Ala
    50                  55                  60

Gly Ala Gly Ala Gly Ala Gly Ala Gly Ala Gly Ala Gly Ala Gly Ala
65                  70                  75                  80

Gly Ala Gly Ala Gly Ala Gly Ala Gly Ala Gly Ala Gly Ala Gly Ala
                85                  90                  95

Gly Ala Gly Ala Gly Ala Gly Ala Gly Ala Gly Ala Gly Ala Gly Ala
            100                 105                 110

Gly Ala Gly Ala Gly Ala Gly Ala Gly Ala Gly Ala Gly Ala Gly Ala
        115                 120                 125

Gly Ala Gly Ala Gly Ala Gly Ala Gly Ala Gly Ala Gly Ala Gly Ala
    130                 135                 140

Gly Ala Gly Ala Gly Ala Gly Ala Gly Ala Gly Ala Gly Ala Gly Ala
145                 150                 155                 160

```
<210> SEQ ID NO 20
<211> LENGTH: 18
<212> TYPE: PRT
<213> ORGANISM: Artificial Sequence
<220> FEATURE:
<223> OTHER INFORMATION: auxiliary amino acid sequence

<400> SEQUENCE: 20

Gly Ala Gly Ala Gly Ser Gly Ala Gly Ala Gly Ser Gly Ala Gly Ala
1               5                   10                  15

Gly Ser

<210> SEQ ID NO 21
<211> LENGTH: 54
<212> TYPE: PRT
<213> ORGANISM: Artificial Sequence
<220> FEATURE:
<223> OTHER INFORMATION: auxiliary amino acid sequence

<400> SEQUENCE: 21

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser
        50

<210> SEQ ID NO 22
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 22

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
            20                  25                  30

Gly Ala Gly Ser Gly Ala Gly Ala Gly Ser Gly Ala Gly Ala Gly Ser
        35                  40                  45

Gly Ala Gly Ala Gly Ser Gly Ala Gly Ala Gly Ser Gly Ala Gly Ala
    50                  55                  60

Gly Ser Gly Ala Gly Ala Gly Ser Gly Ala Gly Ala Gly Ser Gly Ala
65                  70                  75                  80

Gly Ala Gly Ser Gly Ala Gly Ala Gly Ser Gly Ala Gly Ala Gly Ser
                85                  90                  95

Gly Ala Gly Ala Gly Ser Gly Ala Gly Ala Gly Ser Gly Ala Gly Ala
            100                 105                 110

Gly Ser Gly Ala Gly Ala Gly Ser Gly Ala Gly Ala Gly Ser Gly Ala
        115                 120                 125

Gly Ala Gly Ser Gly Ala Gly Ala Gly Ser Gly Ala Gly Ala Gly Ser
    130                 135                 140

Gly Ala Gly Ala Gly Ser Gly Ala Gly Ala Gly Ser Gly Ala Gly Ala
145                 150                 155                 160

Gly Ser Gly Ala Gly Ala Gly Ser Gly Ala Gly Ala Gly Ser Gly Ala
                165                 170                 175

Gly Ala Gly Ser
```

<210> SEQ ID NO 23
<211> LENGTH: 12
<212> TYPE: PRT
<213> ORGANISM: Artificial Sequence
<220> FEATURE:
<223> OTHER INFORMATION: auxiliary amino acid sequence

<400> SEQUENCE: 23

Gly Ala Gly Ala Gly Tyr Gly Ala Gly Ala Gly Tyr
1               5                   10

<210> SEQ ID NO 24
<211> LENGTH: 54
<212> TYPE: PRT
<213> ORGANISM: Artificial Sequence
<220> FEATURE:
<223> OTHER INFORMATION: auxiliary amino acid sequence

<400> SEQUENCE: 24

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
            20                  25                  30

Gly Ala Gly Tyr Gly Ala Gly Ala Gly Tyr Gly Ala Gly Ala Gly Tyr
        35                  40                  45

Gly Ala Gly Ala Gly Tyr
    50

<210> SEQ ID NO 25
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 25

Gly Ala Gly Ala Gly Tyr Gly Ala Gly Ala Gly Tyr Gly Ala Gly Ala
1               5                   10                  15

Gly Tyr Gly Ala Gly Ala Gly Tyr Gly Ala Gly Ala Gly Tyr Gly Ala
            20                  25                  30

Gly Ala Gly Tyr Gly Ala Gly Ala Gly Tyr Gly Ala Gly Ala Gly Tyr
        35                  40                  45

Gly Ala Gly Ala Gly Tyr Gly Ala Gly Ala Gly Tyr Gly Ala Gly Ala
    50                  55                  60

Gly Tyr Gly Ala Gly Ala Gly Tyr Gly Ala Gly Ala Gly Tyr Gly Ala
65                  70                  75                  80

Gly Ala Gly Tyr Gly Ala Gly Ala Gly Tyr Gly Ala Gly Ala Gly Tyr
            85                  90                  95

Gly Ala Gly Ala Gly Tyr Gly Ala Gly Ala Gly Tyr Gly Ala Gly Ala
        100                 105                 110

Gly Tyr Gly Ala Gly Ala Gly Tyr Gly Ala Gly Ala Gly Tyr Gly Ala
    115                 120                 125

Gly Ala Gly Tyr Gly Ala Gly Ala Gly Tyr Gly Ala Gly Ala Gly Tyr
130                 135                 140

Gly Ala Gly Ala Gly Tyr Gly Ala Gly Ala Gly Tyr Gly Ala Gly Ala
145                 150                 155                 160

Gly Tyr Gly Ala Gly Ala Gly Tyr Gly Ala Gly Ala Gly Tyr Gly Ala
            165                 170                 175

Gly Ala Gly Tyr
         180

<210> SEQ ID NO 26
<211> LENGTH: 12
<212> TYPE: PRT
<213> ORGANISM: Artificial Sequence
<220> FEATURE:
<223> OTHER INFORMATION: auxiliary amino acid sequence

<400> SEQUENCE: 26

Gly Ala Gly Val Gly Tyr Gly Ala Gly Val Gly Tyr
1               5                   10

<210> SEQ ID NO 27
<211> LENGTH: 54
<212> TYPE: PRT
<213> ORGANISM: Artificial Sequence
<220> FEATURE:
<223> OTHER INFORMATION: auxiliary amino acid sequence

<400> SEQUENCE: 27

Gly Ala Gly Val Gly Tyr Gly Ala Gly Val Gly Tyr Gly Ala Gly Val
1               5                   10                  15

Gly Tyr Gly Ala Gly Val Gly Tyr Gly Ala Gly Val Gly Tyr Gly Ala
            20                  25                  30

Gly Val Gly Tyr Gly Ala Gly Val Gly Tyr Gly Ala Gly Val Gly Tyr
        35                  40                  45

Gly Ala Gly Val Gly Tyr
    50

<210> SEQ ID NO 28
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 28

Gly Ala Gly Val Gly Tyr Gly Ala Gly Val Gly Tyr Gly Ala Gly Val
1               5                   10                  15

Gly Tyr Gly Ala Gly Val Gly Tyr Gly Ala Gly Val Gly Tyr Gly Ala
            20                  25                  30

Gly Val Gly Tyr Gly Ala Gly Val Gly Tyr Gly Ala Gly Val Gly Tyr
        35                  40                  45

Gly Ala Gly Val Gly Tyr Gly Ala Gly Val Gly Tyr Gly Ala Gly Val
    50                  55                  60

Gly Tyr Gly Ala Gly Val Gly Tyr Gly Ala Gly Val Gly Tyr Gly Ala
65                  70                  75                  80

Gly Val Gly Tyr Gly Ala Gly Val Gly Tyr Gly Ala Gly Val Gly Tyr
                85                  90                  95

Gly Ala Gly Val Gly Tyr Gly Ala Gly Val Gly Tyr Gly Ala Gly Val
            100                 105                 110

Gly Tyr Gly Ala Gly Val Gly Tyr Gly Ala Gly Val Gly Tyr Gly Ala
        115                 120                 125

Gly Val Gly Tyr Gly Ala Gly Val Gly Tyr Gly Ala Gly Val Gly Tyr
    130                 135                 140

Gly Ala Gly Val Gly Tyr Gly Ala Gly Val Gly Tyr Gly Ala Gly Val
145                 150                 155                 160

Gly Tyr Gly Ala Gly Val Gly Tyr Gly Ala Gly Val Gly Tyr Gly Ala
                165                 170                 175

Gly Val Gly Tyr
            180

<210> SEQ ID NO 29
<211> LENGTH: 12
<212> TYPE: PRT
<213> ORGANISM: Artificial Sequence
<220> FEATURE:
<223> OTHER INFORMATION: auxiliary amino acid sequence

<400> SEQUENCE: 29

Gly Ala Gly Tyr Gly Val Gly Ala Gly Tyr Gly Val
1               5                   10

<210> SEQ ID NO 30
<211> LENGTH: 54
<212> TYPE: PRT
<213> ORGANISM: Artificial Sequence
<220> FEATURE:
<223> OTHER INFORMATION: auxiliary amino acid sequence

<400> SEQUENCE: 30

Gly Ala Gly Tyr Gly Val Gly Ala Gly Tyr Gly Val Gly Ala Gly Tyr
1               5                   10                  15

Gly Val Gly Ala Gly Tyr Gly Val Gly Ala Gly Tyr Gly Val Gly Ala
            20                  25                  30

Gly Tyr Gly Val Gly Ala Gly Tyr Gly Val Gly Ala Gly Tyr Gly Val
        35                  40                  45

Gly Ala Gly Tyr Gly Val
        50

<210> SEQ ID NO 31
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 31

Gly Ala Gly Tyr Gly Val Gly Ala Gly Tyr Gly Val Gly Ala Gly Tyr
1               5                   10                  15

Gly Val Gly Ala Gly Tyr Gly Val Gly Ala Gly Tyr Gly Val Gly Ala
            20                  25                  30

Gly Tyr Gly Val Gly Ala Gly Tyr Gly Val Gly Ala Gly Tyr Gly Val
        35                  40                  45

Gly Ala Gly Tyr Gly Val Gly Ala Gly Tyr Gly Val Gly Ala Gly Tyr
    50                  55                  60

Gly Val Gly Ala Gly Tyr Gly Val Gly Ala Gly Tyr Gly Val Gly Ala
65                  70                  75                  80

Gly Tyr Gly Val Gly Ala Gly Tyr Gly Val Gly Ala Gly Tyr Gly Val
                85                  90                  95

Gly Ala Gly Tyr Gly Val Gly Ala Gly Tyr Gly Val Gly Ala Gly Tyr
            100                 105                 110

Gly Val Gly Ala Gly Tyr Gly Val Gly Ala Gly Tyr Gly Val Gly Ala
        115                 120                 125

Gly Tyr Gly Val Gly Ala Gly Tyr Gly Val Gly Ala Gly Tyr Gly Val
    130                 135                 140

Gly Ala Gly Tyr Gly Val Gly Ala Gly Tyr Gly Val Gly Ala Gly Tyr
145                 150                 155                 160

Gly Val Gly Ala Gly Tyr Gly Val Gly Ala Gly Tyr Gly Val Gly Ala

```
                      165                 170                 175

Gly Tyr Gly Val
            180

<210> SEQ ID NO 32
<211> LENGTH: 48
<212> TYPE: PRT
<213> ORGANISM: Artificial Sequence
<220> FEATURE:
<223> OTHER INFORMATION: auxiliary amino acid sequence

<400> SEQUENCE: 32

Asp Gly Gly Ala Ala Ala Ala Ala Gly Gly Ala Asp Gly Gly Ala
1               5                   10                  15

Ala Ala Ala Ala Ala Gly Gly Ala Asp Gly Gly Ala Ala Ala Ala
            20                  25                  30

Ala Gly Gly Ala Asp Gly Gly Ala Ala Ala Ala Ala Gly Gly Ala
        35                  40                  45

<210> SEQ ID NO 33
<211> LENGTH: 18
<212> TYPE: PRT
<213> ORGANISM: Artificial Sequence
<220> FEATURE:
<223> OTHER INFORMATION: auxiliary amino acid sequence

<400> SEQUENCE: 33

Asp Gly Gly Ala Ala Ala Ala Ala Ala Ala Ala Ala Ala Ala Gly
1               5                   10                  15

Gly Ala

<210> SEQ ID NO 34
<211> LENGTH: 72
<212> TYPE: PRT
<213> ORGANISM: Artificial Sequence
<220> FEATURE:
<223> OTHER INFORMATION: auxiliary amino acid sequence

<400> SEQUENCE: 34

Asp Gly Gly Ala Ala Ala Ala Ala Ala Ala Ala Ala Ala Ala Gly
1               5                   10                  15

Gly Ala Asp Gly Gly Ala Ala Ala Ala Ala Ala Ala Ala Ala Ala
            20                  25                  30

Ala Gly Gly Ala Asp Gly Gly Ala Ala Ala Ala Ala Ala Ala Ala
        35                  40                  45

Ala Ala Ala Gly Gly Ala Asp Gly Gly Ala Ala Ala Ala Ala Ala
    50                  55                  60

Ala Ala Ala Ala Ala Gly Gly Ala
65                  70

<210> SEQ ID NO 35
<211> LENGTH: 10
<212> TYPE: PRT
<213> ORGANISM: Artificial Sequence
<220> FEATURE:
<223> OTHER INFORMATION: auxiliary amino acid sequence

<400> SEQUENCE: 35

Gly Val Pro Gly Val Gly Val Pro Gly Val
1               5                   10

<210> SEQ ID NO 36
<211> LENGTH: 50
```

```
<212> TYPE: PRT
<213> ORGANISM: Artificial Sequence
<220> FEATURE:
<223> OTHER INFORMATION: auxiliary amino acid sequence

<400> SEQUENCE: 36

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val
    50

<210> SEQ ID NO 37
<211> LENGTH: 200
<212> TYPE: PRT
<213> ORGANISM: Artificial Sequence
<220> FEATURE:
<223> OTHER INFORMATION: auxiliary amino acid sequence

<400> SEQUENCE: 37

Gly Val Pro Gly Val Gly Val Pro Gly Val Gly Val Pro Gly Val Gly
1               5                   10                  15

Val Pro Gly Val Gly Val Pro Gly Val Gly Val Pro Gly Val Gly Val
            20                  25                  30

Pro Gly Val Gly Val Pro Gly Val Gly Val Pro Gly Val Gly Val Pro
        35                  40                  45

Gly Val Gly Val Pro Gly Val Gly Val Pro Gly Val Gly Val Pro Gly
    50                  55                  60

Val Gly Val Pro Gly Val Gly Val Pro Gly Val Gly Val Pro Gly Val
65                  70                  75                  80

Gly Val Pro Gly Val Gly Val Pro Gly Val Gly Val Pro Gly Val Gly
            85                  90                  95

Val Pro Gly Val Gly Val Pro Gly Val Gly Val Pro Gly Val Gly Val
                100                 105                 110

Pro Gly Val Gly Val Pro Gly Val Gly Val Pro Gly Val Gly Val Pro
        115                 120                 125

Gly Val Gly Val Pro Gly Val Gly Val Pro Gly Val Gly Val Pro Gly
    130                 135                 140

Val Gly Val Pro Gly Val Gly Val Pro Gly Val Gly Val Pro Gly Val
145                 150                 155                 160

Gly Val Pro Gly Val Gly Val Pro Gly Val Gly Val Pro Gly Val Gly
                165                 170                 175

Val Pro Gly Val Gly Val Pro Gly Val Gly Val Pro Gly Val Gly Val
            180                 185                 190

Pro Gly Val Gly Val Pro Gly Val
        195                 200

<210> SEQ ID NO 38
<211> LENGTH: 30
<212> TYPE: PRT
<213> ORGANISM: Artificial Sequence
<220> FEATURE:
<223> OTHER INFORMATION: auxiliary amino acid sequence

<400> SEQUENCE: 38

Gly Val Pro Gly Val Gly Val Pro Gly Val Gly Gly Gly Ala Gly Ala
1               5                   10                  15
```

```
Gly Ser Gly Ala Gly Ala Gly Ser Gly Ala Gly Ala Gly Ser
            20                  25                  30

<210> SEQ ID NO 39
<211> LENGTH: 10
<212> TYPE: PRT
<213> ORGANISM: Artificial Sequence
<220> FEATURE:
<223> OTHER INFORMATION: auxiliary amino acid sequence

<400> SEQUENCE: 39

Gly Gly Gly Gly Gly Gly Gly Gly Gly Gly
1               5                   10

<210> SEQ ID NO 40
<211> LENGTH: 40
<212> TYPE: PRT
<213> ORGANISM: Artificial Sequence
<220> FEATURE:
<223> OTHER INFORMATION: auxiliary amino acid sequence

<400> SEQUENCE: 40

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly
            35                  40

<210> SEQ ID NO 41
<211> LENGTH: 160
<212> TYPE: PRT
<213> ORGANISM: Artificial Sequence
<220> FEATURE:
<223> OTHER INFORMATION: auxiliary amino acid sequence

<400> SEQUENCE: 41

Gly Gly Gly Gly Gly Gly Gly Gly Gly Gly Gly Gly Gly Gly Gly
1               5                   10                  15

Gly Gly Gly Gly Gly Gly Gly Gly Gly Gly Gly Gly Gly Gly Gly
            20                  25                  30

Gly Gly Gly Gly Gly Gly Gly Gly Gly Gly Gly Gly Gly Gly Gly
            35                  40                  45

Gly Gly Gly Gly Gly Gly Gly Gly Gly Gly Gly Gly Gly Gly Gly
        50                  55                  60

Gly Gly Gly Gly Gly Gly Gly Gly Gly Gly Gly Gly Gly Gly Gly
65              70                  75                  80

Gly Gly Gly Gly Gly Gly Gly Gly Gly Gly Gly Gly Gly Gly Gly
            85                  90                  95

Gly Gly Gly Gly Gly Gly Gly Gly Gly Gly Gly Gly Gly Gly Gly
            100                 105                 110

Gly Gly Gly Gly Gly Gly Gly Gly Gly Gly Gly Gly Gly Gly Gly
        115                 120                 125

Gly Gly Gly Gly Gly Gly Gly Gly Gly Gly Gly Gly Gly Gly Gly
    130                 135                 140

Gly Gly Gly Gly Gly Gly Gly Gly Gly Gly Gly Gly Gly Gly Gly
145                 150                 155                 160

<210> SEQ ID NO 42
<211> LENGTH: 10
<212> TYPE: PRT
```

```
<213> ORGANISM: Artificial Sequence
<220> FEATURE:
<223> OTHER INFORMATION: auxiliary amino acid sequence

<400> SEQUENCE: 42

Ala Ala Ala Ala Ala Ala Ala Ala Ala Ala
1               5                   10

<210> SEQ ID NO 43
<211> LENGTH: 40
<212> TYPE: PRT
<213> ORGANISM: Artificial Sequence
<220> FEATURE:
<223> OTHER INFORMATION: auxiliary amino acid sequence

<400> SEQUENCE: 43

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala
            20                  25                  30

Ala Ala Ala Ala Ala Ala Ala Ala
        35                  40

<210> SEQ ID NO 44
<211> LENGTH: 160
<212> TYPE: PRT
<213> ORGANISM: Artificial Sequence
<220> FEATURE:
<223> OTHER INFORMATION: auxiliary amino acid sequence

<400> SEQUENCE: 44

Ala Ala Ala Ala Ala Ala Ala Ala Ala Ala Ala Ala Ala Ala Ala Ala
1               5                   10                  15

Ala Ala Ala Ala Ala Ala Ala Ala Ala Ala Ala Ala Ala Ala Ala Ala
            20                  25                  30

Ala Ala Ala Ala Ala Ala Ala Ala Ala Ala Ala Ala Ala Ala Ala Ala
        35                  40                  45

Ala Ala Ala Ala Ala Ala Ala Ala Ala Ala Ala Ala Ala Ala Ala Ala
    50                  55                  60

Ala Ala Ala Ala Ala Ala Ala Ala Ala Ala Ala Ala Ala Ala Ala Ala
65                  70                  75                  80

Ala Ala Ala Ala Ala Ala Ala Ala Ala Ala Ala Ala Ala Ala Ala Ala
            85                  90                  95

Ala Ala Ala Ala Ala Ala Ala Ala Ala Ala Ala Ala Ala Ala Ala Ala
        100                 105                 110

Ala Ala Ala Ala Ala Ala Ala Ala Ala Ala Ala Ala Ala Ala Ala Ala
    115                 120                 125

Ala Ala Ala Ala Ala Ala Ala Ala Ala Ala Ala Ala Ala Ala Ala Ala
130                 135                 140

Ala Ala Ala Ala Ala Ala Ala Ala Ala Ala Ala Ala Ala Ala Ala Ala
    145                 150                 155                 160

<210> SEQ ID NO 45
<211> LENGTH: 9
<212> TYPE: PRT
<213> ORGANISM: Artificial Sequence
<220> FEATURE:
<223> OTHER INFORMATION: auxiliary amino acid sequence

<400> SEQUENCE: 45

Gly Gly Ala Gly Gly Ala Gly Gly Ala
1               5
```

```
<210> SEQ ID NO 46
<211> LENGTH: 36
<212> TYPE: PRT
<213> ORGANISM: Artificial Sequence
<220> FEATURE:
<223> OTHER INFORMATION: auxiliary amino acid sequence

<400> SEQUENCE: 46

Gly Gly Ala Gly Gly Ala Gly Gly Ala Gly Gly Ala Gly Gly Ala Gly
1               5                   10                  15
Gly Ala Gly Gly Ala Gly Gly Ala Gly Gly Ala Gly Gly Ala Gly Gly
            20                  25                  30
Ala Gly Gly Ala
        35

<210> SEQ ID NO 47
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 47

Gly Gly Ala Gly Gly Ala Gly Gly Ala Gly Gly Ala Gly Gly Ala Gly
1               5                   10                  15
Gly Ala Gly Gly Ala Gly Gly Ala Gly Gly Ala Gly Gly Ala Gly Gly
            20                  25                  30
Ala Gly Gly Ala Gly Gly Ala Gly Gly Ala Gly Gly Ala Gly Gly Ala
        35                  40                  45
Gly Gly Ala Gly Gly Ala Gly Gly Ala Gly Gly Ala Gly Gly Ala Gly
    50                  55                  60
Gly Ala Gly Gly Ala Gly Gly Ala Gly Gly Ala Gly Gly Ala Gly Gly
65                  70                  75                  80
Ala Gly Gly Ala Gly Gly Ala Gly Gly Ala Gly Gly Ala Gly Gly Ala
                85                  90                  95
Gly Gly Ala Gly Gly Ala Gly Gly Ala Gly Gly Ala Gly Gly Ala Gly
            100                 105                 110
Gly Ala Gly Gly Ala Gly Gly Ala Gly Gly Ala Gly Gly Ala Gly Gly
        115                 120                 125
Ala Gly Gly Ala Gly Gly Ala Gly Gly Ala Gly Gly Ala Gly Gly Ala
    130                 135                 140
Gly Gly Ala Gly Gly Ala Gly Gly Ala Gly Gly Ala Gly Gly Ala Gly
145                 150                 155                 160
Gly Ala Gly Gly Ala Gly Gly Ala Gly Gly Ala Gly Gly Ala Gly Gly
                165                 170                 175
Ala Gly Gly Ala
        180

<210> SEQ ID NO 48
<211> LENGTH: 10
<212> TYPE: PRT
<213> ORGANISM: Artificial Sequence
<220> FEATURE:
<223> OTHER INFORMATION: auxiliary amino acid sequence

<400> SEQUENCE: 48

Gly Val Gly Val Pro Gly Val Gly Val Pro
1               5                   10
```

```
<210> SEQ ID NO 49
<211> LENGTH: 50
<212> TYPE: PRT
<213> ORGANISM: Artificial Sequence
<220> FEATURE:
<223> OTHER INFORMATION: auxiliary amino acid sequence

<400> SEQUENCE: 49

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro
    50

<210> SEQ ID NO 50
<211> LENGTH: 200
<212> TYPE: PRT
<213> ORGANISM: Artificial Sequence
<220> FEATURE:
<223> OTHER INFORMATION: auxiliary amino acid sequence

<400> SEQUENCE: 50

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
                20                  25                  30

Gly Val Pro Gly Val Gly Val Pro Gly Val Gly Val Pro Gly Val Gly
            35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
                100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
                180                 185                 190

Gly Val Pro Gly Val Gly Val Pro
            195                 200

<210> SEQ ID NO 51
<211> LENGTH: 9
<212> TYPE: PRT
<213> ORGANISM: Artificial Sequence
<220> FEATURE:
<223> OTHER INFORMATION: auxiliary amino acid sequence

<400> SEQUENCE: 51
```

```
Gly Pro Pro Gly Pro Pro Gly Pro Pro
1               5
```

<210> SEQ ID NO 52
<211> LENGTH: 36
<212> TYPE: PRT
<213> ORGANISM: Artificial Sequence
<220> FEATURE:
<223> OTHER INFORMATION: auxiliary amino acid sequence

<400> SEQUENCE: 52

```
Gly Pro Pro Gly Pro Pro Gly Pro Pro Gly Pro Pro Gly Pro Pro Gly
1               5                   10                  15
Pro Pro Gly Pro Pro Gly Pro Pro Gly Pro Pro Gly Pro Pro Gly Pro
                20                  25                  30
Pro Gly Pro Pro
            35
```

<210> SEQ ID NO 53
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 53

```
Gly Pro Pro Gly Pro Pro Gly Pro Pro Gly Pro Pro Gly Pro Pro Gly
1               5                   10                  15
Pro Pro Gly Pro Pro Gly Pro Pro Gly Pro Pro Gly Pro Pro Gly Pro
                20                  25                  30
Pro Gly Pro Pro Gly Pro Pro Gly Pro Pro Gly Pro Pro Gly Pro Pro
            35                  40                  45
Gly Pro Pro Gly Pro Pro Gly Pro Pro Gly Pro Pro Gly Pro Pro Gly
    50                  55                  60
Pro Pro Gly Pro Pro Gly Pro Pro Gly Pro Pro Gly Pro Pro Gly Pro
65                  70                  75                  80
Pro Gly Pro Pro Gly Pro Pro Gly Pro Pro Gly Pro Pro Gly Pro Pro
                85                  90                  95
Gly Pro Pro Gly Pro Pro Gly Pro Pro Gly Pro Pro Gly Pro Pro Gly
                100                 105                 110
Pro Pro Gly Pro Pro Gly Pro Pro Gly Pro Pro Gly Pro Pro Gly Pro
            115                 120                 125
Pro Gly Pro Pro Gly Pro Pro Gly Pro Pro Gly Pro Pro Gly Pro Pro
    130                 135                 140
Gly Pro Pro Gly Pro Pro Gly Pro Pro Gly Pro Pro Gly Pro Pro Gly
145                 150                 155                 160
Pro Pro Gly Pro Pro Gly Pro Pro Gly Pro Pro Gly Pro Pro Gly Pro
                165                 170                 175
Pro Gly Pro Pro
            180
```

<210> SEQ ID NO 54
<211> LENGTH: 9
<212> TYPE: PRT
<213> ORGANISM: Artificial Sequence
<220> FEATURE:
<223> OTHER INFORMATION: auxiliary amino acid sequence

<400> SEQUENCE: 54

```
Gly Ala Gln Gly Pro Ala Gly Pro Gly
1               5
```

<210> SEQ ID NO 55
<211> LENGTH: 45
<212> TYPE: PRT
<213> ORGANISM: Artificial Sequence
<220> FEATURE:
<223> OTHER INFORMATION: auxiliary amino acid sequence

<400> SEQUENCE: 55

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
            20                  25                  30

Ala Gly Pro Gly Gly Ala Gln Gly Pro Ala Gly Pro Gly
        35                  40                  45

<210> SEQ ID NO 56
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 56

Gly Ala Gln Gly Pro Ala Gly Pro Gly Gly Ala Gln Gly Pro Ala Gly
1               5                   10                  15

Pro Gly Gly Ala Gln Gly Pro Ala Gly Pro Gly Gly Ala Gln Gly Pro
            20                  25                  30

Ala Gly Pro Gly Gly Ala Gln Gly Pro Ala Gly Pro Gly Gly Ala Gln
        35                  40                  45

Gly Pro Ala Gly Pro Gly Gly Ala Gln Gly Pro Ala Gly Pro Gly Gly
    50                  55                  60

Ala Gln Gly Pro Ala Gly Pro Gly Gly Ala Gln Gly Pro Ala Gly Pro
65                  70                  75                  80

Gly Gly Ala Gln Gly Pro Ala Gly Pro Gly Gly Ala Gln Gly Pro Ala
                85                  90                  95

Gly Pro Gly Gly Ala Gln Gly Pro Ala Gly Pro Gly Gly Ala Gln Gly
            100                 105                 110

Pro Ala Gly Pro Gly Gly Ala Gln Gly Pro Ala Gly Pro Gly Gly Ala
        115                 120                 125

Gln Gly Pro Ala Gly Pro Gly Gly Ala Gln Gly Pro Ala Gly Pro Gly
    130                 135                 140

Gly Ala Gln Gly Pro Ala Gly Pro Gly Gly Ala Gln Gly Pro Ala Gly
145                 150                 155                 160

Pro Gly Gly Ala Gln Gly Pro Ala Gly Pro Gly Gly Ala Gln Gly Pro
                165                 170                 175

Ala Gly Pro Gly
            180

<210> SEQ ID NO 57
<211> LENGTH: 15
<212> TYPE: PRT
<213> ORGANISM: Artificial Sequence
<220> FEATURE:
<223> OTHER INFORMATION: auxiliary amino acid sequence

<400> SEQUENCE: 57

Gly Ala Pro Gly Ala Pro Gly Ser Gln Gly Ala Pro Gly Leu Gln
1               5                   10                  15

```
<210> SEQ ID NO 58
<211> LENGTH: 60
<212> TYPE: PRT
<213> ORGANISM: Artificial Sequence
<220> FEATURE:
<223> OTHER INFORMATION: auxiliary amino acid sequence

<400> SEQUENCE: 58

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
            20                  25                  30

Pro Gly Ala Pro Gly Ser Gln Gly Ala Pro Gly Leu Gln Gly Ala Pro
        35                  40                  45

Gly Ala Pro Gly Ser Gln Gly Ala Pro Gly Leu Gln
    50                  55                  60

<210> SEQ ID NO 59
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 59

Gly Ala Pro Gly Ala Pro Gly Ser Gln Gly Ala Pro Gly Leu Gln Gly
1               5                   10                  15

Ala Pro Gly Ala Pro Gly Ser Gln Gly Ala Pro Gly Leu Gln Gly Ala
            20                  25                  30

Pro Gly Ala Pro Gly Ser Gln Gly Ala Pro Gly Leu Gln Gly Ala Pro
        35                  40                  45

Gly Ala Pro Gly Ser Gln Gly Ala Pro Gly Leu Gln Gly Ala Pro Gly
    50                  55                  60

Ala Pro Gly Ser Gln Gly Ala Pro Gly Leu Gln Gly Ala Pro Gly Ala
65                  70                  75                  80

Pro Gly Ser Gln Gly Ala Pro Gly Leu Gln Gly Ala Pro Gly Ala Pro
                85                  90                  95

Gly Ser Gln Gly Ala Pro Gly Leu Gln Gly Ala Pro Gly Ala Pro Gly
            100                 105                 110

Ser Gln Gly Ala Pro Gly Leu Gln Gly Ala Pro Gly Ala Pro Gly Ser
        115                 120                 125

Gln Gly Ala Pro Gly Leu Gln Gly Ala Pro Gly Ala Pro Gly Ser Gln
    130                 135                 140

Gly Ala Pro Gly Leu Gln Gly Ala Pro Gly Ala Pro Gly Ser Gln Gly
145                 150                 155                 160

Ala Pro Gly Leu Gln Gly Ala Pro Gly Ala Pro Gly Ser Gln Gly Ala
                165                 170                 175

Pro Gly Leu Gln
            180

<210> SEQ ID NO 60
<211> LENGTH: 15
<212> TYPE: PRT
<213> ORGANISM: Artificial Sequence
<220> FEATURE:
<223> OTHER INFORMATION: auxiliary amino acid sequence

<400> SEQUENCE: 60

Gly Ala Pro Gly Thr Pro Gly Pro Gln Gly Leu Pro Gly Ser Pro
1               5                   10                  15
```

```
<210> SEQ ID NO 61
<211> LENGTH: 60
<212> TYPE: PRT
<213> ORGANISM: Artificial Sequence
<220> FEATURE:
<223> OTHER INFORMATION: auxiliary amino acid sequence

<400> SEQUENCE: 61

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Pro Gln Gly Leu Pro Gly Ser Pro
    50                  55                  60

<210> SEQ ID NO 62
<211> LENGTH: 180
<212> TYPE: PRT
<213> ORGANISM: Artificial Sequence
<220> FEATURE:
<223> OTHER INFORMATION: auxiliary amino acid sequence

<400> SEQUENCE: 62

Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
            20                  25                  30

Pro Gly Thr Pro Gly Pro Gln Gly Leu Pro Gly Ser Pro Gly Ala Pro
        35                  40                  45

Gly Thr Pro Gly Pro Gln Gly Leu Pro Gly Ser Pro Gly Ala Pro Gly
    50                  55                  60

Thr Pro Gly Pro Gln Gly Leu Pro Gly Ser Pro Gly Ala Pro Gly Thr
65                  70                  75                  80

Pro Gly Pro Gln Gly Leu Pro Gly Ser Pro Gly Ala Pro Gly Thr Pro
                85                  90                  95

Gly Pro Gln Gly Leu Pro Gly Ser Pro Gly Ala Pro Gly Thr Pro Gly
            100                 105                 110

Pro Gln Gly Leu Pro Gly Ser Pro Gly Ala Pro Gly Thr Pro Gly Pro
        115                 120                 125

Gln Gly Leu Pro Gly Ser Pro Gly Ala Pro Gly Thr Pro Gly Pro Gln
    130                 135                 140

Gly Leu Pro Gly Ser Pro Gly Ala Pro Gly Thr Pro Gly Pro Gln Gly
145                 150                 155                 160

Leu Pro Gly Ser Pro Gly Ala Pro Gly Thr Pro Gly Pro Gln Gly Leu
                165                 170                 175

Pro Gly Ser Pro
            180

<210> SEQ ID NO 63
<211> LENGTH: 5
<212> TYPE: PRT
<213> ORGANISM: Homo sapiens

<400> SEQUENCE: 63

Gly Arg Gly Asp Ser
1               5
```

```
-continued
<210> SEQ ID NO 64
<211> LENGTH: 6
<212> TYPE: PRT
<213> ORGANISM: Artificial Sequence
<220> FEATURE:
<223> OTHER INFORMATION: auxiliary amino acid sequence

<400> SEQUENCE: 64

Gly Ala Gly Ala Gly Ser
1               5
```

CELL CULTURE CARRIER COMPRISING POLY(METH)ACRYLIC (SALT) PARTICLE AND ARTIFICIAL POLYPEPTIDE

TECHNICAL FIELD

The present invention relates to a carrier for cell culture, and particularly to a carrier for cell culture which is particularly effective in the cell proliferation of a serum-free culture.

BACKGROUND ART

As a carrier for cell culture, dextran beads having animal-derived collagen (non-patent literature 1), polystyrene beads in which polypeptide having a minimal amino acid sequence which exhibits a cell adhesion signal is provided (patent documents 1), and the like are known.
Non-patent literature 1: Microcarrier cell culture principles & methods (Pharmacia Biotech, published on Oct. 10, 1996), pages 27-31, and the like.
Patent literature 1: JP 2003-189848 A

DISCLOSURE OF THE INVENTION

Problem to be Solved by the Invention

However, the above beads are insufficient in cell proliferativity in serum-free culture. There is also a problem with the above dextran beads in that there is risk of contamination of an infectious factor such as a virus since they contain animal-derived components. That is, an object of the present invention is to provide a carrier for cell culture which improves the cell proliferativity in serum-free culture and which is free from risk of contaminating an infectious factor.

Means for Solving the Problem

The gist of the features of the carrier for cell culture of the present invention is in that the carrier is formed of a crosslinked poly(meth)acrylic acid (salt) particle (A) {this may hereinafter referred to as particle (A)} and an artificial polypeptide (P) having at least one cell-adhesive minimal amino acid sequence (X) in one molecule, and in that the carrier has a water retention value of from 2 to 50 g/g.
The gist of the features of the method for producing a carrier for cell culture of the present invention is in that the method includes a step of mixing a crosslinked poly(meth)acrylic acid (salt) particle (A) with an artificial polypeptide (P) having at least one cell-adhesive minimal amino acid sequence (X) in one molecule in a solvent to obtain the carrier for cell culture, and in that the carrier for cell culture has a water retention value of from 2 to 50 g/g.
The gist of the method for producing a useful substance of the present invention is to include a step of culturing a cell by using the above carrier for cell culture and a serum-free medium.
The gist of the method for producing a tissue or an organ of the present invention is to include a step of culturing a cell by using the above carrier for cell culture and a serum-free medium.

Effect of the Invention

The carrier for cell culture of the present invention demonstrates excellent cell proliferativity. Moreover, it has no risk of contamination of an infectious factor such as a virus since it contains no animal-derived components.

By use of the method for producing a carrier for cell culture of the present invention, it is possible to easily obtain the above carrier for cell culture.
By use of the method for producing a useful substance of the present invention, it is possible to obtain a large amount of a useful substance due to performance of excellent cell proliferativity. Moreover, it is possible to easily obtain a useful substance free from an infectious factor such as a virus.
By use of the method for producing a tissue or an organ of the present invention, it is possible to easily obtain a desired tissue or an organ due to performance of excellent cell proliferativity. Moreover, it is possible to easily obtain a tissue or an organ free from an infectious factor such as a virus.

BEST MODE FOR CARRYING OUT THE INVENTION

Crosslinked poly(meth)acrylic acid (Salt) Particle (A)
The (meth)acrylic acid (salt) means acrylic acid, methacrylic acid, an acrylate, and a methacrylate. As such an acrylate and a methacrylate, alkali metal (lithium, potassium, sodium, and the like) salts, alkaline earth metal (magnesium, calcium, and the like) salts, ammonium salts, and the like of acrylic acid or methacrylic acid are used. Among these, alkali metal salts are preferred, and sodium salts, lithium salts and potassium salts are more preferred. Sodium salts and lithium salts are particularly preferred, and sodium salts are most preferred.

In the crosslinked poly(meth)acrylic acid (salt) particle (A), (meth)acrylic acid (salt) may be copolymerized with other vinyl monomers copolymerizable with (meth)acrylic acid (salt) if the particle contains the (meth)acrylic acid (salt) as a primary constituent unit. Other copolymerizable vinyl monomers include such as copolymerizable monomers (hydrophilic vinyl monomers and hydrophobic vinyl monomers) and crosslinkable monomers.

As the copolymerizable monomers and crosslinkable monomers, conventional products {JP 11-5808 A (counterpart U.S. Pat. No. 5,998,553, the disclosure of which is incorporated herein by reference), JP 2001-2935 A, JP 2003-165883 A, JP 2005-247931 A, JP 2005-186015 A, and the like} can be used.

When using a copolymerizable monomer, the content (% by weight) of copolymerizable monomer units is preferably 0.001 to 10, more preferably 0.01 to 7, particularly preferably 0.03 to 5, and most preferably 0.05 to 3, based on the weight of (meth)acrylic acid (salt) units. From the viewpoint of cell proliferativity, and the like, it is preferable to contain no copolymerizable monomer units.

Among crosslinkable monomers, crosslinkable monomers having two or more ethylenically unsaturated groups and crosslinkable monomers having two or more reactive functional groups are preferable from the viewpoint of cell proliferativity, and the like. Crosslinkable monomers having two or more reactive functional groups are more preferable. Polyethyleneimine, ethylene glycol diglycidyl ether, diethylene glycol diglycidyl ether, propyleneglycol diglycidyl ether, and glycerol (di or tri) glycidyl ether are particularly preferable. Ethylene glycol diglycidyl ether is most preferable.

When using a crosslinkable monomer, the content (% by weight) of crosslinkable monomer units is preferably 0.001 to 50, more preferably 0.005 to 15, particularly preferably 0.02 to 5, and most preferably 0.1 to 2, based on the weight of (meth)acrylic acid (salt) units. When it is within this range, the cell proliferativity is more improved.

The particle (A) can be produced by, for example, a method in which (meth)acrylic acid (salt), as well as if necessary, other copolymerizable vinyl monomers, a polymerization initiator, a chain transfer agent and/or a graft base material are supplied continuously to a hydrophobic organic solvent under stirring to perform conventional reversed phase suspension polymerization {JP 11-5808 A (counterpart U.S. Pat. No. 5,998,553, the disclosure of which is incorporated herein by reference), JP 2001-2935 A, JP 2003-165883 A, JP 2005-247931 A, JP 2005-186015 A, and the like}; a method in which (meth)acrylic acid (salt), as well as if necessary, other copolymerizable vinyl monomers, a polymerization initiator, a chain transfer agent, and/or a graft base material are subjected to conventional aqueous solution polymerization {JP 2005-075982 A, JP 2005-095759 A (counterpart U.S. Patent Application: US 2006/0282052 A1, the disclosure of which is incorporated herein by reference), JP 2005-097569 A, JP 2005-186015 A, JP 2005-186016 A, and the like}.

The crosslinked poly(meth)acrylic acid (salt) particle (A) may be subjected to surface crosslinking treatment with a surface crosslinking agent as needed. From the viewpoint of cell proliferativity, and the like, it is preferable that the vicinity of the surface of the crosslinked poly(meth)acrylic acid (salt) particle is subjected to crosslinking treatment with a surface crosslinking agent.

The surface crosslinking agent includes such as polyvalent glycidyls described in such as JP 59-189103 A (ethylene glycol diglycidyl ether, glycerol diglycidyl ether, and the like are preferred), polyvalent alcohols, polyvalent amines, polyvalent aziridines and polyvalent isocyanates described in such as JP 58-180233 A (counterpart U.S. Pat. No. 4,666,983, the disclosure of which is incorporated herein by reference) and JP 61-16903 A (counterpart U.S. Pat. No. 4,734,478, the disclosure of which is incorporated herein by reference), silane coupling agents described in such as JP 61-211305 A (counterpart U.S. Pat. No. 4,755,560, the disclosure of which is incorporated herein by reference) and JP 61-252212 A, and polyvalent metals described in such as JP 51-136588 A (counterpart U.S. Pat. No. 4,043,952, the disclosure of which is incorporated herein by reference) and JP 61-257235 A. Among such surface crosslinking agents, from the viewpoint of being excellent in heat resistance due to the formation of a strong covalent bond to a carboxyl (salt) group, polyvalent glycidyls, polyvalent amines and silane coupling agents are preferred. More preferred are polyvalent glycidyls and silane coupling agents. Particularly preferred are polyvalent glycidyls.

When performing surface crosslinking treatment, while the amount of the surface crosslinking agent (% by weight) may vary depending upon the kind of the surface crosslinking agent, conditions for crosslinking, and the like, it is preferably 0.002 to 8, more preferably 0.01 to 4, particularly preferably 0.05 to 2, and most preferably 0.05 to 1, based on the weight of the crosslinked poly(meth)acrylic acid (salt) before the surface crosslinking treatment.

As a method for carrying out the surface crosslinking treatment, conventional methods can be applied {for example, JP 11-5808 A (counterpart U.S. Pat. No. 5,998,553, the disclosure of which is incorporated herein by reference), JP 2001-2935 A, JP 2003-165883 A, JP 2005-247931 A, and JP 2005-186015 A}.

The particle (A) is, as needed, subjected to drying treatment, pulverizing treatment and/or classifying treatment. The method of drying treatment is not particularly restricted. For example, a method of drying with hot air at a temperature of 50 to 230° C., a thin film drying method using such as a drum dryer heated to 50 to 230° C., a (heat) vacuum drying method, a freeze drying method, and a drying method using infrared radiation can be employed. The method of pulverizing treatment is not particularly restricted. Pulverization can be done by, for example, use of an ordinary apparatus (hammer type pulverizers, impact type pulverizers, roll type pulverizers, jet stream type pulverizers, and the like). The method of classifying treatment is not also particularly restricted. Classification can be done by use of an ordinary apparatus (dry vibrating screens, wet vibrating screens, air classifiers, and the like).

The external shape of the particle (A) may be any of spherical shape, needle shape, flattened (ellipse) shape (fusiform), thin flake shape, grape bunch shape, amorphous pulverized shape, and fibrous shape. However, from the viewpoint of cell proliferativity, and the like, spherical shape and flattened (ellipse) shape (fusiform) are preferred, and spherical shape is more preferred. That is, a preferable form of the particle (A) is beads.

From the viewpoint of cell proliferativity and the like, the volume average particle diameter ($\mu$m) of swollen particles obtained by swelling particles (A) with physiological saline is preferably 10 $\mu$m to 2000 $\mu$m, more preferably 25 $\mu$m to 1000 $\mu$m, particularly preferably 50 $\mu$m to 500 $\mu$m, and most preferably 100 $\mu$m to 300 $\mu$m.

Here, the volume average particle diameter of the swollen particles can be determined by measuring swollen particles prepared by immersing 1 part by weight of particles (A) in 100 parts by weight of physiological saline (0.9% by weight) at 25° C. for 60 minutes by means of a laser type particle size distribution analyzer (for example, LA-920 manufactured by HORIBA, Ltd.; dispersion medium: physiological saline, measurement temperature: 25° C.) in accordance with JIS Z8825-1: 2001 {counterpart International Standard: ISO13320-1:1999 "particle size analysis—Laser diffraction methods—Part 1: General principles": the disclosure of which is incorporated herein by reference}.

From the viewpoint of cell proliferativity and the like, the water retention value (g/g) of the particle (A) to physiological saline is preferably 2 to 50, more preferably 5 to 40, particularly preferably 10 to 30, and most preferably 10 to 25.

The water retention value is measured by the following method. To a beaker containing about 100 mL of physiological saline, 1.0 g of dry crosslinked poly(meth)acrylic acid (salt) particles are added under stirring and are caused to swell previously to obtain swollen particles. Then, the particles are transferred into a tea bag (20 cm in length, 10 cm in width) made of a nylon net having 53 $\mu$m openings, followed by immersion in excess physiological saline for 60 minutes. Subsequently, the swollen particles are put into a centrifugal dehydrator together with the tea bag, followed by being subjected to centrifugal dehydration at 150 G for 90 seconds. Thus, the excessive water is removed. The weight (g2) after the centrifugal dehydration is measured, and the value calculated from the following formula is defined as a water retention value (reference: JIS K7223-1996). Here, the dry crosslinked poly(meth)acrylic acid (salt) particles are obtains by drying undried particles under conditions of 120° C. and 0.1 kPa or less for one hour.

$$(\text{Water retention value}) = (g2) - 1.0$$

The particle (A) can be obtained easily from the market and can include AQUAPEARL series {San-Dia Polymers Ltd.}, SANFRESH series {Sanyo Chemical Industries, Ltd.}, AQUA KEEP series {Sumitomo Seika Chemicals Co., Ltd.}, ARONZAP series (Toagosei Co. Ltd.), and AQUALIC series (Nippon Shokubai Co., Ltd.). Among these, AQUAPEARL series and AQUA KEEP series are preferred, and AQUA-PEARL series is more preferred. Here, it is noted that "AQUAPEARL", "SANFRESH", "AQUA KEEP", "ARONZAP" and "AQUALIC" are registered trademarks in Japan (as to some of these trademarks, corresponding trademarks in English are registered in U.S., China, and the like).
Artificial Polypeptide (P)

"Cell adhesiveness" means a property that a specific minimal amino acid sequence is recognized by an integrin receptor of a cell, so that the cell becomes more adhesive to a substrate (Osaka Medical Center and Research Institute for Maternal and Child Health magazine, Vol. 8, No. 1, pp. 58-66, 1992).

As the cell-adhesive minimal amino acid sequence (X), such as those described in "Pathophysiology, Vol. 9, No. 7, pp. 527-535, 1990" and "Osaka Medical Center and Research Institute for Maternal and Child Health magazine, Vol. 8, No. 1, pp. 58-66, 1992" are used.

Among such minimal amino acid sequences (X), preferred is at least one kind of sequence selected from the group consisting of an Arg Gly Asp sequence, a Leu Asp Val sequence, a Leu Arg Glu sequence, a His Ala Val sequence, an Arg Glu Asp Val sequence (1), a Tyr Ile Gly Ser Arg sequence (2), a Pro Asp Ser Gly Arg sequence (3), an Arg Tyr Val Val Leu Pro Arg sequence (4), a Leu Gly Thr Ile Pro Gly sequence (5), an Arg Asn Ile Ala Glu Ile Ile Lys Asp Ile sequence (6), an Ile Lys Val Ala Val sequence (7), an Asp Gly Glu Ala sequence (8), a Gly Val Lys Gly Asp Lys Gly Asn Pro Gly Trp Pro Gly Ala Pro sequence (9), a Gly Glu Phe Tyr Phe Asp Leu Arg Leu Lys Gly Asp Lys sequence (10), a Tyr Lys Leu Asn Val Asn Asp Ser sequence (11), an Ala Lys Pro Ser Tyr Pro Pro Thr Tyr Lys sequence (12), an Asn Arg Trp His Ser Ile Tyr Ile Thr Arg Phe Gly sequence (13), a Thr Trp Tyr Lys Ile Ala Phe Gln Arg Asn Arg Lys sequence (14), an Arg Lys Arg Leu Gln Val Gln Leu Ser Ile Arg Thr (15), and a Pro His Ser Arg Asn (16). From the viewpoint of cell adhesiveness, and the like more preferred is at least one kind of sequence selected from the group consisting of the Arg Gly Asp sequence, the Tyr Ile Gly Ser Arg sequence (2), the Ile Lys Val Ala Val sequence (7), the Arg Lys Arg Leu Gln Val Gln Leu Ser Ile Arg Thr (15), and the Pro His Ser Arg Asn (16). The Arg Gly Asp sequence is particularly preferred.

Such minimal amino acid sequences (X) may have, at their both ends, other amino acids {alanine (Ala), glycine (Gly), serine (Ser), threonine (Thr), valine (Val), leucine (Leu), isoleucine (Ile), cysteine (Cys), methionine (Met), phenylalanine (Phe), thyroxin (Tyr), proline (Pro), tryptophan (Trp), asparagine (Asn), glutamine (Gln), aspartic acid (Asp), glutamic acid (Glu), arginine (Arg), lysine (Lys), histidine (His), and the like}.

The artificial polypeptide (P) is required to have at least one minimal amino acid sequence (X) in one molecule. From the viewpoint of cell adhesiveness, however, it preferably has 1 to 50, more preferably 2 to 50, even more preferably 3 to 30, particularly preferably 4 to 20, and most preferably 5 to 15 minimal amino acid sequences. Two or more kinds of minimal amino acid sequences (X) may be contained in one molecule.

From the viewpoint of improvement in the thermal stability of the artificial polypeptide (P), the artificial polypeptide (P) preferably contains an auxiliary amino acid sequence (Y) other than minimal amino acid sequences (X).

As the auxiliary amino acid sequence (Y), an amino acid sequence other than minimal amino acid sequences (X) may be used. From the viewpoint of the thermal stability of the artificial polypeptide (P), sequences having Gly and/or Ala are preferred. The auxiliary amino acid sequence (Y) includes such as sequences having a (Gly Ala)a sequence, a (Gly Ala Gly Ala Gly Ser)b sequence, a (Gly Ala Gly Ala Gly Tyr)c sequence, a (Gly Ara Gly Val Gly Tyr)d sequence, a (Gly Ala Gly Tyr Gly Val)e sequence, an {Asp Gly Gly (Ala)f Gly Gly Ala}g sequence, a (Gly Val Pro Gly Val)h sequence, a (Gly)i sequence, an (Ala)j sequence, a (Gly Gly Ala)k sequence, a (Gly Val Gly Val Pro)m sequence, a (Gly Pro Pro)n sequence, a (Gly Ala Gln Gly Pro Ala Gly Pro Gly)o sequence, a (Gly Ala Pro Gly Ala Pro Gly Ser Gln Gly Ala Pro Gly Leu Gln)p sequence and/or a (Gly Ala Pro Gly Thr Pro Gly Pro Gln Gly Leu Pro Gly Ser Pro)q sequence. Among these preferred are sequences having the (Gly Ala)a sequence, the (Gly Ala Gly Ala Gly Ser)b sequence, the (Gly Ala Gly Ala Gly Tyr)c sequence, the (Gly Ala Gly Val Gly Tyr)d sequence, the (Gly Ala Gly Tyr Gly Val) e, the {Asp Gly Gly (Ala)f Gly Gly Ala}g sequence, the (Gly Val Pro Gly Val)h sequence, the (Gly Val Gly Val Pro)m sequence and/or the (Gly Pro Pro)n sequence. More preferred are sequences having the (Gly Ala Gly Ala Gly Ser)b sequence, the (Gly Val Pro Gly Val)h sequence, the (Gly Val Gly Val Pro)m sequence and/or the (Gly Pro Pro)n sequence. Particularly preferred are sequences having the (Gly Ala Gly Ala Gly Ser)b sequence.

Here, it is noted that a is an integer from 5 to 100, b is an integer from 1 to 33, c, d and e are each an integer from 2 to 33, f is an integer from 1 to 194, g is {1} to an integer obtained by omitting the figures below the decimal point of {200/(6+f)}, h is an integer from 2 to 40, i and j are each an integer from 10 to 200, k is an integer from 3 to 66, m is an integer from 2 to 40, n is an integer from 3 to 66, o is an integer from 1 to 22, and p and q are each an integer from 1 to 13.

The auxiliary amino acid sequence (Y) preferably contains glycine (Gly) and/or alanine (Ala). When glycine (Gly) and alanine (Ala) are contained, the percentage of the total content thereof (%) is preferably from 10 to 100, more preferably from 20 to 95, particularly preferably from 30 to 90, and most preferably from 40 to 85 based on the number of all amino acids in the auxiliary amino acid sequence. When it is within this range, the thermal stability is better.

When both glycine (Gly) and alanine (Ala) are contained, the ratio of the contained numbers thereof (Gly/Ala) is preferably from 0.03 to 40, more preferably from 0.08 to 13, and particularly preferably from 0.2 to 5. When it is within this range, the thermal stability is better.

The auxiliary amino acid sequences (Y) may contain other amino acids {alanine (Ala), glycine (Gly), serine (Ser), threonine (Thr), valine (Val), leucine (Leu), isoleucine (Ile), cysteine (Cys), methionine (Met), phenylalanine (Phe), thyroxin (Tyr), proline (Pro), tryptophan (Trp), asparagine (Asn), glutamine (Gln), aspartic acid (Asp), glutamic acid (Glu), arginine (Arg), lysine (Lys), histidine (His), and the like} besides the above examples.

The auxiliary amino acid sequence having the (Gly Ala)a sequence includes amino acid sequences represented by sequence No. (17) to (19).

The auxiliary amino acid sequence having the (Gly Ala Gly Ala Gly Ser)b sequence includes amino acid sequences represented by sequence No. (20) to (22).

The auxiliary amino acid sequence having the (Gly Ala Gly Ala Gly Tyr)c sequence includes amino acid sequences represented by sequence No. (23) to (25).

The auxiliary amino acid sequence having the (Gly Ala Gly Val Gly Tyr)d sequence includes amino acid sequences represented by sequence No. (26) to (28).

The auxiliary amino acid sequence having the (Gly Ala Gly Tyr Gly Val)e sequence includes amino acid sequences represented by sequence No. (29) to (31).

The auxiliary amino acid sequence having the {Asp Gly Gly (Ala)f Gly Gly Ala}g sequence includes amino acid sequences represented by sequence No. (32) to (34).

The auxiliary amino acid sequence having the (Gly Val Pro Gly Val)h sequence includes amino acid sequences represented by sequence No. (35) to (38).

The auxiliary amino acid sequence having the (Gly)i sequence includes amino acid sequences represented by sequence No. (39) to (41).

The auxiliary amino acid sequence having the (Ala)j sequence includes amino acid sequences represented by sequence No. (42) to (44).

The auxiliary amino acid sequence having the (Gly Gly Ala)k sequence includes amino acid sequences represented by sequence No. (45) to (47).

The auxiliary amino acid sequence having the (Gly Val Gly Val Pro)m sequence includes amino acid sequences represented by sequence No. (48) to (50).

The auxiliary amino acid sequence having the (Gly Pro Pro)n sequence includes amino acid sequences represented by sequence No. (51) to (53).

The auxiliary amino acid sequence having the (Gly Ala Gln Gly Pro Ala Gly Pro Gly)o sequence includes amino acid sequences represented by sequence No. (54) to (56).

The auxiliary amino acid sequence having the (Gly Ala Pro Gly Ala Pro Gly Ser Gln Gly Ala Pro Gly Leu Gln)p sequence includes amino acid sequences represented by sequence No. (57) to (59).

The auxiliary amino acid sequence having the (Gly Ala Pro Gly Thr Pro Gly Pro Gln Gly Leu Pro Gly Ser Pro)q sequence includes amino acid sequences represented by sequence No. (60) to (62).

Among these auxiliary amino acid sequences, an amino acid sequence represented by sequence No. (17), (18), (20), (21), (22), (23), (24), (26), (27), (29), (30), (32), (33), (34), (35), (36), (38), (39), (40), (42), (43), (45), (46), (48), (49), (51), (52), (54), (55), (57), (58), (60), or (61) is preferred. An amino acid sequence represented by sequence No. (18), (20), (21), (22), (24), (27), (30), (34), (35), (36), (37), (38), (40), (43), (46), (49), (52), (55), (58), or (61) is more preferred, and an amino acid sequence represented by sequence No. (20), (21), or (38) is particularly preferred.

When containing an auxiliary amino acid sequence (Y), the number of (Y) contained in one molecule of the artificial polypeptide (P) is preferably 2 to 50, more preferably 3 to 30, particularly preferably 4 to 20, and most preferably 5 to 15, from the viewpoint of thermal stability and the like. The artificial polypeptide (P) may also contain two or more kinds of auxiliary amino acid sequences (Y).

The artificial polypeptide (P) may contain a branched chain, and may be partially crosslinked, and may contain a cyclic structure. However, the artificial polypeptides (P) is not preferably crosslinked, more preferably has an uncrosslinked straight chain structure, and particularly preferably has no cyclic structure and has an uncrosslinked straight structure. Here, it is noted that a straight chain structure includes a β structure (a secondary structure in which a straight chain peptide is folded and the sections thereof are set in parallel to each other and a hydrogen bond is formed therebetween).

From the viewpoint of cell adhesiveness and thermal stability, the artificial polypeptide (P) preferably has a structure in which a minimal amino acid sequence (X) and an auxiliary amino acid sequence (Y) are chemically bonded alternately. In this case, from the cell adhesiveness point of view, the number of the repeating units (X-Y) of the minimal amino acid sequence (X) and the auxiliary amino acid sequence (Y) is preferably 1 to 50, more preferably 2 to 40, particularly preferably 3 to 30, and most preferably 4 to 20.

The number of the minimal amino acid sequences (X) and the auxiliary amino acid sequences (Y) may be the same or different. When they are different, it is preferable that any of the number is one smaller than the other number {in this case, it is preferable that the auxiliary amino acid sequences (Y) be fewer}. The ratio (X/Y) of the number of the minimal amino acid sequences (X) to the number of the auxiliary amino acid sequences (Y) contained in the artificial polypeptide (P) is preferably from 0.5 to 2, more preferably from 0.9 to 1.4, and particularly preferably from 1 to 1.3.

The artificial polypeptide (P) may have other amino acids at a terminal portion thereof (a portion from the minimal amino acid sequence (X) or the auxiliary amino acid sequence (Y) to the end of the peptide). When other amino acids are contained, the number thereof is preferably 1 to 1,000, more preferably 3 to 300, and particularly preferably 10 to 100 per one molecule of the artificial polypeptide (P).

The weight average molecular weight (hereinafter, Mw) of the artificial polypeptide (P) is preferably 1,000 to 1,000,000, more preferably 2,000 to 700,000, particularly preferably 3,000 to 400,000, and most preferably 4,000 to 200,000. Here, the Mw of the artificial polypeptide (P) is measured by a conventional method, such as a method in which a sample for measurement (polypeptide, and the like) is separated by the SDS-PAGE (SDS polyacrylamide gel electrophoresis) method, followed by comparison of migration distance with a standard substance (the same shall apply hereinafter).

Some examples of preferable artificial polypeptides (P) are shown below.

(1) The Minimal Amino Acid Sequence (X) is an Arg Gly Asp Sequence (x1)

A polypeptide having an Mw of about 110,000 which has a structure in which 13 Arg Gly Asp sequences (x1) and 12 (Gly Ala Gly Ala Gly Ser)$_9$ sequences (21) (y1) are chemically bonded alternately {"ProNectin F", ProNectin is a registered trademark (in Japan and U.S.) of Sanyo Chemical Industries, Ltd., produced by Sanyo Chemical Industries, Ltd.<the same shall apply hereinafter>}; a polypeptide having an Mw of about 20,000 which has a structure in which five (x1)s and five (Gly Ala Gly Ala Gly Ser)$_3$ sequences (20) (y2) are chemically bonded alternately ("ProNectin F2"); and a polypeptide having an Mw of about 10,000 which has a structure in which three (x1)s and three (Gly Val Pro Gly Val)$_2$ Gly Gly (Gly Ala Gly Ala Gly Ser)$_3$ sequences (38) (y3) are chemically bonded alternately ("ProNectin F3").

(2) The Minimal Amino Acid Sequence (X) is Ile Lys Val Ala Val Sequence (x2)

"ProNectin L", "ProNectin L2", "ProNectin L3" or the like which is obtained by changing the Arg Gly Asp sequence (x1) in ProNectin F, ProNectin F2, or ProNectin F3 to the Ile Lys Val Ala Val sequence (7) (x2).

(3) The Minimal Amino Acid Sequence (X) is an Tyr Ile Gly Ser Arg sequence (x3)

"ProNectin Y", "ProNectin Y2", "ProNectin Y3" or the like which is obtained by changing the Arg Gly Asp sequence (x1) in ProNectin F, ProNectin F2, or ProNectin F3 to a Tyr Ile Gly Ser Arg sequence (x3).

Besides the polypeptides (1)-(3), there may be also preferably used RetroNectin (Recombinant Human Fibronectin CH-296) produced by Takara Shuzo Co., Ltd. {a polypeptide having an Mw of about 60,000 which contains the Arg Gly Asp sequence (x1) and an Leu Asp Val sequence as the minimal amino acid sequence (X)}, and RGDS-Protein A produced by Takara Shuzo Co., Ltd. {a polypeptide having an Mw of about 30,000 which contains the Arg Gly Asp sequence (x1) as the minimal amino acid sequence (X)}. Here, these polypeptides are naturally occurring and do not contain the auxiliary amino acid sequence (Y). Therefore, the thermal resistance and the like thereof are inferior to those of the above (1) to (3). Moreover, the amino acid sequences of these polypeptides are disclosed in JP 2-311498 A (counterpart U.S. patent is U.S. Pat. No. 5,198,423, the disclosure of which is incorporated herein by reference).

The artificial polypeptide (P) is a product synthesized artificially; it is produced, for example, by an organic synthesis method, such as a solid phase synthesis method or a liquid phase synthesis method, a biochemical synthesis method [genetic recombinant bacteria (such as yeast, bacteria, and *E. coli*)], or the like. That is, the artificial polypeptide (P) excludes cellular adhesive proteins, such as collagen, fibronectin, or the like derived from animals.

Regarding the organic synthesis method, there may be used, for example, a method described in "Zoku Seikagaku Jikken Koza 2, Tanpakushitsu No Kagaku (Ge) (Lectures on Biochemical Experiments 2, Chemistry of Proteins Vol. 2)" pages 641-694, edited by The Japanese Biochemical Society, (published by Tokyo Kagaku Dojin; May 20, 1987) and the like. Regarding the biochemical synthesis method, there may be used, for example, a method described in JP 3-502935 T (the counterpart International Patent Appliation: WO90/05177, the disclosure of which is incorporated herein by reference) and the like. From the viewpoint of being able to readily synthesize the artificial polypeptide (P), a biochemical synthesis method using genetic recombinant bacteria is preferred, and particularly preferred is a synthesis method using genetic recombinant *E. coli*.

In the carrier for cell culture of the present invention, the particle (A) and the artificial polypeptide (P) are bonded together usually by chemical bonding (such as ionic bonding, hydrogen bonding, and/or covalent bonding) and/or physical adsorption (adsorption by Van der Waals force). From the viewpoint that a particle (A) and an artificial polypeptide (P) are bonded firmly, chemical bonding is preferred, and more preferred is covalent bonding.

The method for covalently bonding an artificial polypeptide (P) to a particle (A) includes the methods described in "Peptide Gosei no Kiso to Jikken (Fundamentals and Experiments of Peptide Synthesis)" published by Maruzen (Oct. 5, 1997). More specifically, these are (1) to (3) shown below.

(1) When an artificial polypeptide (P) having a primary amino group or a secondary amino group is caused to react with a carboxyl group of a particle (A), the carboxyl group is previously caused to react with a carbodiimide compound to obtain an acylisourea {R'—N=C(OCOR)—NH—R' (—OCOR is a site derived from the carrier for cell culture)}. Then, the artificial polypeptide having a primary amino group or a secondary amino group is added to the acylisourea, so that the particle (A) and the artificial polypeptide (P) can be amide bonded. The carbodiimide compound includes such as N,N'-dicyclohexylcarbodiimide and 1-ethyl-3-(3-dimethylaminopropyl)carbodiimide hydrochloride.

(2) When an artificial polypeptide (P) having a primary amino group or a secondary amino group is caused to react with a particle (A) having a hydroxyl group {using a hydroxyl group-containing monomer as a copolymerized monomer}, the hydroxyl group of the particle (A) is previously caused to react with a carbonyldiimidazole compound to obtain an imidazole derivative {R-Im, where Im denotes an imidazoline ring and R is derived from the particle (A)}. Then, the artificial polypeptide (P) having a primary amino group or a secondary amino group is added to the imidazole derivative, so that the particle (A) and the artificial polypeptide (P) can be N—C bonded. The carbonyldiimidazole compound includes such as N,N'-carbonyldiimidazole.

(3) When an artificial polypeptide (P) having a hydroxyl group is caused to react with a carboxyl group of a particle (A), the carboxyl group of the particle (A) is previously caused to react with a carbodiimide compound to obtain an acylisourea. Then, the artificial polypeptide (P) having a hydroxyl group is added to the acylisourea, so that the particle (A) and the polypeptide can be ester bonded.

The methods of physically adsorbing, ionically bonding and/or hydrogen-bonding an artificial polypeptide (P) to a particle (A) include a production method including charging the artificial polypeptide (P) and the particle (A) into a solvent and the like and mixing them. While the solvent is not specifically restricted, there may be used such as an aqueous solution containing inorganic salt, organic acid salt, acid and/or base in an amount of 0.01 to 50% by weight (preferably 0.005 to 30% by weight, and more preferably 0.01 to 10% by weight) (described in JP 2003-189848 A and the like). Among such solvents, aqueous solutions containing inorganic salt, acid and/or base and water are preferred, aqueous solutions containing inorganic salt, acid and/or base and ion exchanged distilled water are more preferred, and aqueous solutions containing inorganic salt, acid and/or base are particularly preferred.

From the viewpoint of improvement in cell adhesiveness, the content of the artificial polypeptide (P) is preferably 5 ng/g to 500 mg/g, more preferably 50 ng/g to 50 mg/g, further preferably 500 ng/g to 50 mg/g, further preferably 500 ng/g to 20 mg/g, particularly preferably 500 ng/g to 5 mg/g, and most preferably 5 µg to 5 mg/g based on dry weight of the carrier for cell culture.

Here, the content of the artificial polypeptide (P) based on dry unit weight of the carrier for cell culture is determined by, for example, the Biuret method {"Seikagaku Jikken Koza, volume 1, Tanpakushitsu no Kagaku I (Lecture of Biochemical Experiments Vol. 1, Protein Chemistry 1)", edited by The Japanese Biochemical Society, pp. 45-55 (Dec. 11, 1979; Tokyo Kagaku Dojin Co., Ltd.) and the like, when the content of the artificial polypeptide (P) is more than 500 µg/g.

On the other hand, when the content of the artificial polypeptide (P) is 500 µg/g or less, it is determined by, for example, the Kjeldahl method {"Seikagaku Jikken Koza, volume 1, Tanpakushitsu no Kagaku I (Lecture of Biochemical Experiments Vol. 1, Protein Chemistry 1)", edited by The Japanese Biochemical Society, pp. 45-55 (Dec. 11, 1979; Tokyo Kagaku Dojin Co., Ltd.} and the like.

It can also be measured by using an immunoassay method (described in JP 2004-049921 and the like). Specifically, (1) a carrier for cell culture in which the content of the artificial polypeptide (P) is known {a carrier for cell culture in which the content of the artificial polypeptide (P) has been known by the Biuret method, the Kjeldahl method or the like} is immersed in physiological saline, and then it is caused to react with an enzyme-labeled antibody which can bond to the artificial polypeptide (P). The amount of enzyme of the reacted enzyme-labeled antibody is determined by absorbance measurement to produce a calibration curve (content of artificial polypeptide (P) versus absorbance). (2) In a similar manner, a sample (a carrier for cell culture in which the content of the artificial polypeptide (P) is unknown) is measured for absorbance. Based on the calibration curve obtained in (1) and the absorbance measured in (2), the content of the artificial polypeptide (P) of the sample can be determined. The dry weight can be obtained by putting 1 g of a sample into a vacuum dryer, drying the sample for 1 hour under conditions of 120° C., 0.1 kPa or lower, and then weighing the sample.

The carrier for cell culture of the present invention may contain a cell growth factor in order to improve the cell proliferativity. The cell growth factor include substances which promote the growth of cells, such as biologically active polypeptide, e.g. fibroblast growth factor, transforming growth factor, epidermal growth factor, hepatocyte growth factor, platelet derived growth factor, insulin like growth factor, vascular endothelial cell growth factor, nerve growth factor, stem cell factor, leukemia inhibitory factor, bone morphogenetic factor, heparin-binding epidermal growth factor, neurotrophic factor, connective tissue growth factor, angiopoietin, chondromodulin, tenomodulin, interferon, interleukin, tumor necrosis factor, colony stimulating factor, adrenamodulin, natriuretic peptide and the like {for example, described in "Tissue Engineering edited by Minoru UEDA" published by The University of Nagoya Press (1999)}. From the viewpoint of being applicable to a wide variety of tissue cells and increasing cell proliferativity, a fibroblast growth factor, a transforming growth factor, an epidermal growth factor, a hepatocyte growth factor, a platelet derived growth factor, an insulin like growth factor, a vascular endothelial cell growth factor, a bone morphogenetic protein, interleukin, and a tumor necrosis factor are preferred among those cell growth factors. More preferred are the fibroblast growth factor, the epidermal growth factor, the insulin like growth factor, the vascular endothelial cell growth factor, interleukin, and the tumor necrosis factor.

The cell growth factor is preferably bonded to the particle (A). Similar to the bonding between the particle (A) and the artificial polypeptide (P), this bonding may be employed chemical binding and/or physical adsorption. Preferable chemical bond and/or physical adsorption are also similar to those described before.

When the cell growth factor is contained, the content thereof is preferably 10 pg/g to 1000 μg/g, more preferably 100 pg/g to 100 μg/g, and particularly preferably 1000 pg/g to 10 μg/g based on dry weight of the carrier for cell culture, from the viewpoint of improving cell proliferativity.

Preferable ranges of the external shape, volume average particle diameter and water retention value of the carrier for cell culture of the present invention are consistent with the preferable ranges of the particle (A).

The carrier for cell culture of the present invention may be subjected to sterilization treatment as needed. As the sterilization method, sterilization methods using radiation, ethylene oxide gas, plasma, γ ray, alcohol, an autoclave, dry heat or the like may be applied. These may be performed alone or in combination of two or more kinds.

There are no particular restrictions with the cell (CE) which can be adhered to the carrier for cell culture of the present invention as long as it is a cell. However, because high cell proliferativity is obtained when the carrier for cell culture of the present invention is used, suitable are normal cells derived from mammalian, cell lines derived from mammalian, and insect cells which are used for the production of useful substances such as medicaments or the like, therapies, or the like.

The normal cells derived from mammalian include such as cells involved in the skin (epithelial cells, fibroblasts, vascular endothelial cells, smooth muscle cells and the like), cells involved in blood vessels (vascular endothelial cells, smooth muscle cells, fibroblasts and the like), cells involved in muscles (muscle cells and the like), cells involved in adipo (adipocytes and the like), cells involved in nerves (neurocytes and the like), cells involved in livers (hepatocytes and the like), cells involved in pancreas (pancreatic islet cells of Langerhans and the like), cells involved in kidneys (renal epithelial cells, renal proximal tubular epithelial cells, mesangial cells and the like), cells involved in lungs and bronchial tubes (epithelial cells, fibroblasts, vascular endothelial cells, smooth muscle cells and the like), cells involved in eyes (visual cells, corneal epithelial cells, corneal endothelial cells and the like), cells involved in prostate glands (epithelial cells, interstitial cells, smooth muscle cells and the like), cells involved in bones (osteoblasts, osteocytes, osteoclasts and the like), cells involved in cartilages (chondroblasts, chondrocytes and the like), cells involved in teeth (periodontium cells, osteoblasts and the like), cells involved in blood (leucocytes, erythrocytes and the like), and stem cells {e.g., bone marrow undifferentiated mesenchymal stem cells, skeletal muscle stem cells, hematopoietic stem cells, neural stem cells, liver stem cells (oval cells, small hepatocytes and the like), adipo tissue stem cells, embryonic stem (ES) cells, epidermal stem cells, intestinal stem cells, sperm stem cells, embryonic germline (EG) stem cells, pancreas stem cells (pancreatic epithelial stem cells and the like), leukocytic stem cells, lymphoid stem cell, corneal stem cells, and precursor cells (preadipocytes, vascular endothelial precursor cells, cartilage precursor cells, lymphoid precursor cells, NK precursor cells and the like)}

The cell lines derived from mammalian include such as 3T3 cells, 549 cells, AH130 cells, B95-8 cells, BHK cells, BOSC23 cells, BS-C-1 cells, C3H10T1/2 cells, C-6 cells, CHO cells, COS cells, CV-1 cells, F9 cells, FL cells, FL5-1 cells, FM3 A cells, G-361 cells, GP+E-86 cells, GP+envAm12 cells, H4-11-E cells, HEK293 cells, HeLa cells, HEp-2 cells, HL-60 cells, HTC cells, HUVEC cells, IMR-32 cells, IMR-90 cells, K562 cells, KB cells, L cells, L5178Y cells, L-929 cells, MA104 cells, MDBK cells, MDCK cells, MIAPaCa-2 cells, N18 cells, Namalwa cells, NG108-15 cells, NRK cells, OC10 cells, OTT6050 cells, P388 cells, PA12 cells, PA317 cells, PC-12 cells, PER. C6 cells, PG13 cells, QGH cells, Raji cells, RPMI-1788 cells, SGE1 cells, Sp2/O—Ag14 cells, ST2 cells, THP-1 cells, U-937 cells, V79 cells, VERO cells, WI-38 cells, ψ2 cells, and ψCRE cells, {Saibo Baiyo no Gijutsu "Techniques of Cell Culture" (edited by The Japan Tissue Culture Association, published by Asakura Publishing Co., Ltd., 1999)}.

The insect cells include silkworm cells (BmN cell, BoMo cell and the like), *Bombyx* mandarina cells, perny silk moth cells, cynthia silk moth cells, cabbage army worm cells, (Sf9 cell, Sf21 cell and the like), mulberry tiger moth cells, tortrix cells, *drosophila* cells, *sarcophaga peregrina* cells, Stegomyia mosquito cells, swallowtail butterfly cells, *Periplaneta americana* cell, and *Trichoplusia ni* cell (Tn-5 cell, HIGH FIVE cell, MG1 cell and the like) {Konchu Baio Kojo (Insect Biofactory) (edited by Kimura Shigeru, published by Kogyo chosakai Publishing, Inc., 2000)}.

Among such cells, the normal cells derived from mammalian and the cell lines derived from mammalian are preferable from the viewpoint of production of useful substances such as medicaments and the like, therapies and the like. From the viewpoint of being useful for therapies, more preferred are the smooth muscle cell hepatocytes, the osteoblasts, the epithelial cells, the fibroblasts, the vascular endothelial cells, and the stem cells, and particularly preferred are the epithelial cells.

From the viewpoint of being useful for production of useful substances such as medicaments, more preferred are the 3T3 cells, the BHK cells, the CHO cells, the HEK293 cells, the HeLa cells, the L-929 cells, the MDCK cells, the PER. C6 cells, the VERO cells, and the WI-38 cells, and particularly preferred are the MDCK cells and the VERO cells.

The medium (ME) to be used a cell culture method using the carrier for cell culture of the present invention includes a serum-free media (Grace's medium, IPL-41 medium, Schneider's medium, Opti-PRO™ SFM medium, Opti- MEM™ I medium, VP-SFM medium, CD293 medium, 293SFMII medium, CD-CHO medium, CHO-S-SFMII medium, FreeStyle™ 293 medium, CD-CHO ATG™ media, and mixed media thereof); general medium (RPMI medium, MEM medium, Eagle's MEM medium, BME medium, DME medium, α (alpha) MEM medium, IMEM medium, ES medium, DM-160 medium, Fisher medium, F12 medium, WE medium, ASF103 medium, ASF104 medium, ASF301 medium, TC-100 medium, Sf-90011 medium, Ex-cell405 medium, Express-Five medium, *Drosophila* medium, and mixed media thereof); and mixed media thereof.

From the viewpoint of preventing contamination of substances with possibility of infection to human (serum-derived virus and the like), the serum-free medium is preferred. More preferred are Opti-PRO™ SFM medium, Opti-MEM™ I medium, VP-SFM medium, CD293 medium, 293SFMII medium, CD-CHO medium, CHO-S-SFMII medium, FreeStyle™ 293 medium, CD-CHO ATG™ medium, and mixed media thereof. Particularly preferred are Opti-PRO™ SFM medium, VP-SFM medium, CD293 medium, 293SFMII medium, FreeStyle™ 293 medium, and mixed media thereof.

While serum may be added to such media, it is preferable not to add serum from the viewpoint of preventing contamination of substances with possibility of infection to human (serum-derived virus and the like). Such serum includes human serum and animal serum (bovine serum, horse serum, goat serum, sheep serum, pig serum, rabbit serum, fowl serum, rat serum, mouse serum and the like). When adding serum, the human serum, the bovine serum, and the horse serum are preferred. The animal-derived serum includes adult-derived serum, fetus-derived serum, neonate-derived serum, and embryo-derived serum. When adding serum, the fetus-derived serum, the neonate-derived serum, and the embryo-derived serum are preferred. More preferred are the neonate-derived serum and the embryo-derived serum, and particularly preferred is the embryo-derived serum. When adding serum, the serum may be subjected to inactivation treatment, antibody removal treatment or the like. When using serum, the used amount of the serum (% by weight) is preferably 0.1 to 50, more preferably 0.3 to 30, and particularly preferably 1 to 20 based on the weight of the medium.

A cell growth factor may be contained in the medium as needed. By causing the medium to contain the cell growth factor, it is possible to increase the proliferation rate of cells or to increase the cell activity. Such cell growth factors include biologically active peptides, such as a fibroblast growth factor, a transforming growth factor, an epidermal growth factor, a hepatocyte growth factor, a platelet derived growth factor, an insulin like growth factor, a vascular endothelial growth factor, a nerve growth factor, a stem cell factor, a leukemia inhibitory factor, a bone morphogenetic protein, a heparin-binding epidermal growth factor, a neurotrophic factor, a connective tissue growth factor, angiopoietin, cytokine, interleukin, adrenamodulin, and natriuretic peptide. From the viewpoint of being applicable to a wide variety of cells and being capable of shortening the curing period, preferred are the fibroblast growth factor, the transforming growth factor, the insulin like growth factor, and the bone morphogenetic protein, and more preferred are the fibroblast growth factor, the transforming growth factor, and the insulin like growth factor. In the case of using the cell growth factor, while the content (% by weight) of the cell growth factor varies depending on the kind of the cell growth factor, it is preferably $10^{-16}$ to $10^{-3}$, more preferably $10^{-14}$ to $10^{-5}$, and particularly preferably $10^{-12}$ to $10^{-7}$ based on the weight of the medium.

Such a medium may further be caused to contain an antimicrobial agent (amphotericin B, gentamicin, penicillin, streptomycin and the like). When causing the medium to contain an antimicrobial agent, while the content thereof (% by weight) may vary depending upon the kind of the antimicrobial agent, it is preferably $10^{-6}$ to 10, more preferably $10^{-5}$ to 1, and particularly preferably $10^{-4}$ to 0.1 based on the weight of the medium.

While the concentration of cells to be dispersed in the medium (cells/mL) is not particularly limited, it is preferably 100 to 100,000,000, more preferably 1,000 to 10,000,000, and particularly preferably 10,000 to 1000,000 per milliliter of medium. As the method for counting the number of cells, conventional methods may be used. For example, it can be counted by a cell nuclei-counting method using crystal violet {Saibo Baiyo no Gijutsu "Techniques of Cell Culture" (edited by The Japan Tissue Culture Association, published by Asakura Publishing Co., Ltd., 1999)}.

While the dry weight (g) of the carrier for cell culture to be charged to a medium may be determined properly depending upon, for example, the kind of the cell to be cultured, it is preferably 0.005 to 800, more preferably 0.02 to 200, and particularly preferably 0.1 to 40 per liter of medium.

The culture condition is not particularly restricted, and conditions can be applied where culture is performed at carbon dioxide ($CO_2$) concentration of 1 to 20 vol %, at 5 to 45° C., for 1 hour to 100 days, as needed while exchanging the medium every one to ten days. Preferable conditions are conditions where culture is performed at $CO_2$ concentration of 3 to 10 vol %, at 30 to 40° C., for 1 to 20 days while exchanging the medium every one to three days.

As a method for exfoliating cells from a carrier for cell culture, conventional methods may be used. For example, there may be used a method of exfoliating cells with chelating agents (EDTA and the like), proteolytic enzymes derived from non-animals {proteolytic enzymes derived from vegetables (papain and the like)}, synthetic enzymes by gene recombination (e.g., trade name: TrypLE™ Select, produced by Invitrogen Corporation.), and/or proteolytic enzymes derived from animals (trypsin, collagenase and the like).

EXAMPLES

The present invention is hereafter further described with reference to Examples, but the invention is not limited to the Examples only. Unless otherwise stated, part(s) and % mean part(s) by weight and % by weight, respectively.

Example 1

Preparation of Crosslinked Polyacrylic Acid Salt Particle (A1)

Into a reaction vessel equipped with a stirrer, a monomer feeding tube, a nitrogen gas introducing tube, a thermometer, and a reflux condenser, 624 parts of cyclohexane and 3.1 parts of sorbitan monostearate as a polymerization dispersing agent were charged, and then nitrogen bubbling was performed for 30 minutes or more to expel the dissolved air, followed by raising the temperature to 75° C.

Into another reactor, 173 parts of 80% aqueous acrylic acid solution was charged, and then it was neutralized by addition of 207 parts of 28% aqueous sodium hydroxide solution under cooling. To the resulting aqueous solution, 4.52 parts of a crosslinkable monomer (ethylene glycol diglycidyl ether), 0.278 part a polymerization initiator (potassium persulfate) and 0.053 part of a chain transfer agent (sodium hypophosphite) were added, and then nitrogen bubbling was performed to expel the dissolved air, thereby obtaining an aqueous monomer solution.

The resulting aqueous monomer solution was fed into the cyclohexane solution under stirring (the stirring speed was 500 rpm) in the polymerization reaction vessel through the monomer feeding tube of the polymerization reaction vessel, continuously at a rate of 6.5 mL/min over about one hour, and polymerization was performed under cyclohexane reflux. Subsequently, after removal of 160 parts of water by azeotropic dehydration, a water-containing gel polymer was taken out, followed by drying at 120° C. for 2 hours to obtain dry crosslinked polyacrylic acid sodium salt. The dry crosslinked polyacrylic acid sodium salt was classified with a 63 gra sieve and a 53 µm sieve {JIS Z8801-1:2000 (counterpart International Standard ISO 3310-1 "Test sieves—Technical requirements and testing Part 1: Test sieves of metal wire cloth": the disclosure of which is incorporated herein by reference}} to yield particles (crosslinked polyacrylic acid sodium salt particles) having a particle diameter of from 53 to 63 µm. Then, 7.5 parts of a methanol/ion exchange water (70/30 in volume ratio) solution containing ethylene glycol diglycidyl ether at solution concentration of 2% was added to the resulting particles, followed by mixing uniformly. Subsequently, after air-drying methanol, the residue was charged into a closed container and held at 80° C. for one hour, thereby being subjected to surface crosslinking. Then, the matter was dried at 120° C. for 30 minutes in a fair wind dryer to yield the crosslinked polyacrylic acid salt particle (A1).

Preparation of Artificial Polypeptide (P1)

In accordance with the description of an example in JP 3-502935 T (counterpart International Patent Application; WO90/05177, the disclosure of which is incorporated herein by reference), a peptide "ProNectin F" having an Mw of about 110,000 which had a structure in which 13 Arg Gly Asp sequences and 12 (Gly Ala Gly Ala Gly Ser) 9 sequences (21) are chemically bonded alternately was produced. This was used as an artificial polypeptide (P1).

Preparation of Carrier for Cell Culture (C1)

To 1 g of crosslinked polyacrylic acid salt particle (A1), 50 mL of a 0.02 M, pH 7.2 phosphate buffer (hereinafter, PBS) containing 0.85% of sodium chloride was added, followed by being left at rest for 30 minutes to swell the crosslinked polyacrylic acid salt particle (A1). Then, excess PBS was removed by suction with an aspirator. After addition thereto of 40 mL of a PBS solution containing a water-soluble carbodiimide (1-ethyl-3-(3-dimethylaminopropyl)carbodiimide hydrochloride, produced by Dojindo Laboratories) at concentration of 60 mM, stirring with a stirring blade made of polyfluoroethylene resin was performed to continue a reaction for two hours. After suction removal of the reaction solution, a washing operation composed of addition of 40 mL of PBS and suction removal thereof was repeated five times.

Then, after addition thereto of 40 mL of a PBS solution containing the artificial polypeptide (P1) at concentration of 600 µg/mL, stirring with a stirring blade made of polyfluoroethylene resin was performed to continue a reaction for two hours. After suction removal of the reaction solution, a washing operation composed of addition of 40 mL of PBS and suction removal thereof was repeated five times. Moreover, a washing operation composed of addition of 40 mL of ion exchange water and suction removal thereof was repeated twice.

Finally, the resultant was placed in a vacuum dryer, and was subjected to drying under the condition at 120° C. and 0.1 kPa or less for 4 hours to yield a carrier for cell culture (C1) of the present invention. The water retention value of the carrier (C1) was 13 g/g. The carrier (C1) contained 2 mg/g of the artificial polypeptide (P1). The content of the artificial polypeptide was measured by immunological determination method using a calibration curve produced by the Biuret method. It is noted that in the event that the content was expected to be 500 µg or less, a calibration curve produced by the Kjeldahl method was used {the same shall apply hereinafter}.

Example 2

A crosslinked polyacrylic acid salt particle (A2) and a carrier for cell culture (C2) were obtained in the same manner as Example 1 except for (changing the used amount of the crosslinkable monomer, ethylene glycol diglycidyl ether, in the polymerization from 4.52 parts to 1.81 parts). The water retention value of the carrier (C2) was 18 g/g. The carrier (C2) contained 4 mg/g of the artificial polypeptide (P1).

Example 3

A crosslinked polyacrylic acid salt particle (A3) and a carrier for cell culture (C3) were obtained in the same manner as Example 1 except for (changing the used amount of the crosslinkable monomer, ethylene glycol diglycidyl ether, in the polymerization from 4.52 parts to 0.90 part). The water retention value of the carrier (C3) was 21 g/g. The carrier (C3) contained 5 mg/g of the artificial polypeptide (P1).

Example 4

A crosslinked polyacrylic acid salt particle (A4) and a carrier for cell culture (C4) were obtained in the same manner as Example 1 except for (changing the used amount of the crosslinkable monomer, ethylene glycol diglycidyl ether, in the polymerization from 4.52 parts to 0.09 part). The water retention value of the carrier (C4) was 23 g/g. The carrier (C4) contained 6 mg/g of the artificial polypeptide (P1).

Example 5

A crosslinked polyacrylic acid salt particle (A3) and a carrier for cell culture (C5) were obtained in the same manner as Example 1 except for (changing the used amount of the crosslinkable monomer, ethylene glycol diglycidyl ether, in the polymerization from 4.52 parts to 0.90 part) and (using an artificial polypeptide (P2) {a polypeptide "ProNectin F2" having an Mw of about 20,000 which was prepared in accordance with the method described in an Example in JP 3-502935 T and which had a structure where five Arg Gly Asp sequences (x1) and five (Gly Ala Gly Ala Gly Ser)$_3$ sequences (20) (y2) were chemically bonded alternately} instead of the artificial polypeptide (P1)). The water retention value of the carrier (C5) was 21 g/g. The carrier (C5) contained 2 mg/g of the artificial polypeptide (P2).

Example 6

A crosslinked polyacrylic acid salt particle (A3) and a carrier for cell culture (C6) were obtained in the same manner as Example 1 except for (changing the used amount of the crosslinkable monomer, ethylene glycol diglycidyl ether, in the polymerization from 4.52 parts to 0.90 part) and (using an artificial polypeptide (P3) {a polypeptide "ProNectin F3" having an Mw of about 10,000 which was prepared in accordance with the method described in an Example in JP 3-502935 T and which had a structure where three Arg Gly Asp sequences (x1) and three (Gly Val Pro Gly Val)$_2$ Gly Gly (Gly Ala Gly Ala Gly Ser)$_3$ sequences (38) (y3) were chemically bonded alternately} instead of the artificial polypeptide (P1)). The water retention value of the carrier (C6) was 21 g/g. The carrier (C6) contained 1 mg/g of the artificial polypeptide (P3).

Example 7

A crosslinked polyacrylic acid salt particle (A3) and a carrier for cell culture (C7) were obtained in the same manner as Example 1 except for (changing the used amount of the crosslinkable monomer, ethylene glycol diglycidyl ether, in the polymerization from 4.52 parts to 0.90 part) and (using an artificial polypeptide (P4) {a polypeptide having an Mw of 490 which had an Arg Gly Asp sequence (x1); Gly Arg Gly Asp Ser sequence (63), produced by Peptide Institute, Inc.} instead of the artificial polypeptide (P1)). The water retention value of the carrier (C7) was 21 g/g. The carrier (C7) contained 0.1 mg/g of artificial polypeptide (P4).

Example 8

A particle (crosslinked polyacrylic acid sodium salt particle) was obtained in the same manner as Example 1 except for (changing the used amount of the crosslinkable monomer, ethylene glycol diglycidyl ether, in the polymerization from 4.52 parts to 0.90 part). This particle was used as a crosslinked polyacrylic acid salt particle (A5) without being subjected to surface crosslinking treatment. A carrier for cell culture (C8) was obtained in the same manner as Example 1 except for (using crosslinked polyacrylic acid salt particle (A5) instead of crosslinked polyacrylic acid salt particle (A1) in the preparation of a carrier for cell culture). The water retention value of the carrier (C8) was 22 g/g. The carrier (C8) contained 5 mg/g of the artificial polypeptide (P1).

Example 9

Preparation of Artificial Polypeptide (P5)

(1) Preparation of Artificial Polypeptide (P5A)

In accordance with the DCC method described such as in "Peptide gosei no kiso to jikken (Fundamentals and Experiments in Peptide Synthesis), Maruzen, Ltd. (Jan. 20, 1985), pp. 114-117, a solution was prepared which contained, at concentration of about 5%, a crosslinked polypeptide obtained by causing the artificial polypeptides (P4) themselves to react. After filtration of 10 mL of the solution through a 0.45 µm membrane filter, the filtrate was fractioned with a gel filtration column (trade name: Superdex 30 pg, manufactured by Amersham Biosciences Corporation (General Electric Company)) to obtain a fraction with an Mw of about 1,000 {flow rate: 1 mL/min, eluent: PBS; a fraction with an Mw of about 1,000 was separated with reference to the elution time of a molecular weight marker which had been gel fractioned previously under the same conditions). The fraction with an Mw of about 1,000 was dialyzed in ion exchange water to desalt, and then it was freeze-dried for 24 hours under the conditions of −20° C. and 0.1 kPa or less to obtain an artificial polypeptide (P5A) {having about two Gly Arg Gly Asp Ser sequences (63)}.

(2) Preparation of Artificial Polypeptide (P5C)

An artificial polypeptide (P5B) {having about four Gly Arg Gly Asp Ser sequences (63)} was obtained in the same manner as the preparation of the artificial polypeptide (P5A) except for (causing the artificial polypeptides (P5A) themselves to react instead of causing the artificial polypeptides (P4) themselves to react), and (separating a fraction with an Mw of about 2,000 instead of the fraction with an Mw of about 1,000).

Subsequently, an artificial polypeptide (P5C) {having about eight Gly Arg Gly Asp Ser sequences (63)} was obtained in the same manner as the preparation of the artificial polypeptide (P5A) except for (causing the artificial polypeptides (P5B) themselves to react instead of causing the artificial polypeptides (P4) themselves to react), and (separating a fraction with an Mw of about 4,000 instead of the fraction with an Mw of about 1,000).

(3) Preparation of Artificial Polypeptide (P5)

An artificial polypeptide (P5) {having about 10 Gly Arg Gly Asp Ser sequences (63)} was obtained in the same manner as the preparation of the artificial polypeptide (P5A) except for (causing the artificial polypeptide (P5A) and the artificial polypeptide (P5C) to react at a molar ratio of 1:1 instead of causing the artificial polypeptides (P4) themselves to react), and (separating a fraction with an Mw of about 5,000 instead of the fraction with an Mw of about 1,000).

Preparation of Carrier for Cell Culture (C9)

A crosslinked polyacrylic acid salt particle (A3) and a carrier for cell culture (C9) were obtained in the same manner as Example 1 except for (changing the used amount of the crosslinkable monomer, ethylene glycol diglycidyl ether, in the polymerization from 4.52 parts to 0.90 part) and (using the artificial polypeptide (P5) instead of the artificial polypeptide (P1)). The water retention value of the carrier (C9) was 21 g/g. The carrier (C9) contained 0.5 mg/g of the artificial polypeptide (P5).

Example 10

Preparation of Artificial Polypeptide (P6)

An artificial polypeptide (P6) {having about 20 Gly Arg Gly Asp Ser sequences (63)} was obtained in the same manner as Example 9(1) except for (causing the artificial polypeptides (P5) themselves to react instead of causing the artificial polypeptides (P4) themselves to react), (using trade name: Superdex 75 pg as a gel filtration column instead of using trade name: Superdex 30 pg), and (separating a fraction with an Mw of about 10,000 instead of the fraction with an Mw of about 1,000).

Preparation of Carrier for Cell Culture (C10)

A crosslinked polyacrylic acid salt particle (A3) and a carrier for cell culture (C10) were obtained in the same manner as Example 1 except for (changing the used amount of the crosslinkable monomer, ethylene glycol diglycidyl ether, in the polymerization from 4.52 parts to 0.90 part) and (using the artificial polypeptide (P6) instead of the artificial polypeptide (P1)). The water retention value of the carrier (C10) was 21 g/g. The carrier (C10) contained 2 mg/g of the artificial polypeptide (P6).

Example 11

Preparation of Artificial Polypeptide (P7)

An artificial polypeptide (P7) {having about 30 Gly Arg Gly Asp Ser sequences (63)} was obtained in the same manner as Example 9(1) except for (causing the artificial polypeptide (P5) and the artificial polypeptide (P6) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 15,000 instead of the fraction with an Mw of about 1,000).

Preparation of Carrier for Cell Culture (C11)

A crosslinked polyacrylic acid salt particle (A3) and a carrier for cell culture (C11) were obtained in the same manner as Example 1 except for (changing the used amount of the crosslinkable monomer, ethylene glycol diglycidyl ether, in the polymerization from 4.52 parts to 0.90 part) and (using the artificial polypeptide (P7) instead of the artificial polypeptide (P1)). The water retention value of the carrier (C11) was 21 g/g. The carrier (C11) contained 2 mg/g of the artificial polypeptide (P7).

Example 12

Preparation of Artificial Polypeptide (P8)

An artificial polypeptide (P8) {having about 40 Gly Arg Gly Asp Ser sequences (63)} was obtained in the same manner as Example 9(1) except for (causing the artificial polypeptides (P6) themselves to react instead of causing the artificial polypeptides (P4) themselves to react), (using trade name: Superdex 75 pg as a gel filtration column instead of using trade name: Superdex 30 pg), and (separating a fraction with an Mw of about 20,000 instead of the fraction with an Mw of about 1,000).

Preparation of Carrier for Cell Culture (C12)

A crosslinked polyacrylic acid salt particle (A3) and a carrier for cell culture (C12) were obtained in the same manner as Example 1 except for (changing the used amount of the crosslinkable monomer, ethylene glycol diglycidyl ether, in the polymerization from 4.52 parts to 0.90 part) and (using the artificial polypeptide (P8) instead of the artificial polypeptide (P1)). The water retention value of the carrier (C12) was 21 g/g. The carrier (C12) contained 3 mg/g of the artificial polypeptide (P8).

Example 13

Preparation of Artificial Polypeptide (P9)

An artificial polypeptide (P9) {having about one Gly Arg Gly Asp Ser sequence (63) and about one Gly Ala Gly Ala Gly Ser sequence (64)} was obtained in the same manner as Example 9(1) except for (causing the artificial polypeptide (P4) and a polypeptide composed of Gly Ala Gly Ala Gly Ser sequence (64) to react at a molar ratio of 1:1 instead of causing the artificial polypeptides (P4) themselves to react).

Preparation of Carrier for Cell Culture (C13)

A crosslinked polyacrylic acid salt particle (A3) and a carrier for cell culture (C13) were obtained in the same manner as Example 1 except for (changing the used amount of the crosslinkable monomer, ethylene glycol diglycidyl ether, in the polymerization from 4.52 parts to 0.90 part) and (using the artificial polypeptide (P9) instead of the artificial polypeptide (P1)). The water retention value of the carrier (C13) was 21 g/g. The carrier (C13) contained 0.2 mg/g of the artificial polypeptide (P9).

Example 14

Preparation of Artificial Polypeptide (P10)

(1) Preparation of Artificial Polypeptide (P10A)
An artificial polypeptide (P10A) {having about two Gly Ala Gly Ala Gly Ser sequences (64)} was obtained in the same manner as Example 9(1) except for (causing the Gly Ala Gly Ala Gly Ser sequences (64) themselves to react instead of causing the artificial polypeptides (P4) themselves to react).
(2) Preparation of Artificial Polypeptide (P10D)
An artificial polypeptide (P10B) {having about four Gly Ala Gly Ala Gly Ser sequences (64)} was obtained in the same manner as Example 9(1) except for (causing the artificial polypeptides (P10A) themselves to react instead of causing the artificial polypeptides (P4) themselves to react), and (separating a fraction with an Mw of about 2,000 instead of the fraction with an Mw of about 1,000).

Subsequently, an artificial polypeptide (P10C) {having about eight Gly Ala Gly Ala Gly Ser sequences (64)} was obtained in the same manner as Example 9(1) except for (causing the artificial polypeptides (P10B) themselves to react instead of causing the artificial polypeptides (P4) themselves to react), and (separating a fraction with an Mw of about 3,000 instead of the fraction with an Mw of about 1,000).

Subsequently, an artificial polypeptide (P10D) {having about 10 Gly Ala Gly Ala Gly Ser sequences (64)} was obtained in the same manner as Example 9(1) except for (causing the artificial polypeptide (P10A) and the artificial polypeptide (P10C) to react at a molar ratio of 1:1 instead of causing the artificial polypeptides (P4) themselves to react), and (separating a fraction with an Mw of about 4,000 instead of the fraction with an Mw of about 1,000).
(3) Preparation of Artificial Polypeptide (P10)
An artificial polypeptide (P10) {having about one Gly Arg Gly Asp Ser sequence (63) and about 10 Gly Ala Gly Ala Gly Ser sequences (64)} was obtained in the same manner as Example 9(1) except for (causing the artificial polypeptide (P4) and the artificial polypeptide (P10D) to react at a molar ratio of 1:1 instead of causing the artificial polypeptides (P4) themselves to react), and (separating a fraction with an Mw of about 5,000 instead of the fraction with an Mw of about 1,000).

Preparation of Carrier for Cell Culture (C14)

A crosslinked polyacrylic acid salt particle (A3) and a carrier for cell culture (C14) were obtained in the same manner as Example 1 except for (changing the used amount of the crosslinkable monomer, ethylene glycol diglycidyl ether, in the polymerization from 4.52 parts to 0.90 part) and (using the artificial polypeptide (P10) instead of the artificial polypeptide (P1)). The water retention value of the carrier (C14) was 21 g/g. The carrier (C14) contained 0.3 mg/g of the artificial polypeptide (P10).

Example 15

Preparation of Artificial Polypeptide (P11)

An artificial polypeptide (P11A) {having about 20 Gly Ala Gly Ala Gly Ser sequences (64)} was obtained in the same manner as Example 9(1) except for (causing the artificial polypeptides (P10D) themselves to react instead of causing the artificial polypeptides (P4) themselves to react), and (separating a fraction with an Mw of about 8,000 instead of the fraction with an Mw of about 1,000.) was obtained.

Subsequently, an artificial polypeptide (P11) {having about one Gly Arg Gly Asp Ser sequence (63) and about 20 Gly Ala Gly Ala Gly Ser sequences (64)} was obtained in the same manner as Example 9(1) except for (causing the artificial polypeptide (P4) and the artificial polypeptide (P11A) to react at a molar ratio of 1:1 instead of causing the artificial polypeptides (P4) themselves to react), and (separating a fraction with an Mw of about 9,000 instead of the fraction with an Mw of about 1,000).

Preparation of Carrier for Cell Culture (C15)

A crosslinked polyacrylic acid salt particle (A3) and a carrier for cell culture (C15) were obtained in the same manner as Example 1 except for (changing the used amount of the crosslinkable monomer, ethylene glycol diglycidyl ether, in the polymerization from 4.52 parts to 0.90 part) and (using the artificial polypeptide (P11) instead of the artificial polypeptide (P1)). The water retention value of the carrier (C15) was 21 g/g. The carrier (C15) contained 1 mg/g of the artificial polypeptide (P11).

Example 16

Preparation of Artificial Polypeptide (P12)

An artificial polypeptide (P12A) {having about 30 Gly Ala Gly Ala Gly Ser sequences (64)} was obtained in the same manner as Example 9(1) except for (causing the artificial polypeptide (P10D) and the artificial polypeptide (P11A) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 13,000 instead of the fraction with an Mw of about 1,000).

Subsequently, an artificial polypeptide (P12) {having about one Gly Arg Gly Asp Ser sequence (63) and about 30 Gly Ala Gly Ala Gly Ser sequences (64)} was obtained in the same manner as Example 9(1) except for (causing the artificial polypeptide (P4) and the artificial polypeptide (P12A) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 13,000 instead of the fraction with an Mw of about 1,000).

Preparation of Carrier for Cell Culture (C16)

A crosslinked polyacrylic acid salt particle (A3) and a carrier for cell culture (C16) were obtained in the same manner as Example 1 except for (changing the used amount of the crosslinkable monomer, ethylene glycol diglycidyl ether, in the polymerization from 4.52 parts to 0.90 part) and (using the artificial polypeptide (P12) instead of the artificial polypeptide (P1)). The water retention value of the carrier (C16) was 21 g/g. The carrier (C16) contained 2 mg/g of the artificial polypeptide (P12).

Example 17

Preparation of Artificial Polypeptide (P13)

An artificial polypeptide (P13A) {having about 50 Gly Ala Gly Ala Gly Ser sequences (64)} was obtained in the same manner as Example 9(1) except for (causing the artificial polypeptide (P11A) and the artificial polypeptide (P12A) to react at a molar ratio of 1:1 instead of causing the artificial polypeptides (P4) themselves to react), (using trade name: Superdex 75 pg as a gel filtration column instead of using trade1 name: Superdex 30 pg), and (separating a fraction with an Mw of about 21,000 instead of the fraction with an Mw of about 1,000).

Subsequently, an artificial polypeptide (P13) {having about one Gly Arg Gly Asp Ser sequence (63) and about 50 Gly Ala Gly Ala Gly Ser sequences (64)} was obtained in the same manner as Example 9(1) except for (causing the artificial polypeptide (P4) and the artificial polypeptide (P13A) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 21,000 instead of the fraction with an Mw of about 1,000).

Preparation of Carrier for Cell Culture (C17)

A crosslinked polyacrylic acid salt particle (A3) and a carrier for cell culture (C17) were obtained in the same manner as Example 1 except for (changing the used amount of the crosslinkable monomer, ethylene glycol diglycidyl ether, in the polymerization from 4.52 parts to 0.90 part) and (using the artificial polypeptide (P13) instead of the artificial polypeptide (P1)). The water retention value of the carrier (C17) was 21 g/g. The carrier (C17) contained 2 mg/g of the artificial polypeptide (P13).

Example 18

Preparation of Crosslinked Polyacrylic Acid Salt Particle (A6)

A mixture of 88 parts of sodium acrylate, 22.85 parts of acrylic acid, 0.2 part of N,N'-methylenebisacrylamide, 293 parts of deionized water, and 0.001 part of dichlorotris(triphenylphosphine)ruthenium was held at 1 to 2° C. while being stirred and mixed. Then, nitrogen was blown into the mixed liquid to adjust the dissolved oxygen concentration in the mixed liquid to 0.5 ppm or less. Subsequently, to the mixed liquid, 0.3 part of 1% aqueous hydrogen peroxide solution, 0.8 part of 0.2% aqueous ascorbic acid solution, and 0.8 part of 2% aqueous 2,2'-azobis(amidinopropane) dihydrochloride solution were added and mixed to initialize polymerization. After the reaction liquid reached 80° C., the polymerization was performed at a polymerization temperature of 80±2° C. for about five hours to obtain a water-containing resin (gel). Using a mincing machine (hole diameter of perforated plate: 6 mm, "12VR-400K" manufactured by Iizuka Kogyo k.k.), 400 parts of the water-containing resin (gel) was minced at 25° C. for five minutes, and then dried in a through-flow band type drier manufactured by Inoue Kinzoku Kogyo CO. LTD. at 135° C. and 2.0 m/sec to obtain a dry polymer. This dry polymer was pulverized with a juicer mixer (National MX-X53, manufactured by Matsushita Electric Industrial Co.) and then classified with a 63 μm sieve and a 53 μm sieve (JIS Z8801-1:2000) to obtain particles {crosslinked polyacrylic acid sodium salt particles} having a particle diameter from 53 to 63 μm. While stirring 100 parts of the particles at high speed ("High-speed stirring turbulizer mixer" manufactured by Hosokawa Micron Corporation, rate of revolution: 2000 rpm), 1 part of 1% ethylene glycol diglycidyl ether solution in water/methanol mixture (weight ratio of water/methanol=60/40) was added and mixed by spraying. The mixture was left at rest at 140° C. for 30 minutes to be subjected to crosslink (surface crosslink) by heating, and thereby a crosslinked polyacrylic acid salt particle (A6) was obtained.

Preparation of Carrier for Cell Culture (C18)

A carrier for cell culture (C18) was obtained in the same manner as Example 1 except for (using the crosslinked polyacrylic acid salt particle (A6) instead of the crosslinked polyacrylic acid salt particle (A1)). The water retention value of the carrier (C18) was 21 g/g. The carrier (C18) contained 10 mg/g of the artificial polypeptide (P1).

Example 19

A crosslinked polyacrylic acid salt particle (A7) and a carrier for cell culture (C19) were obtained in the same manner as Example 1 except for (changing the used amount of the 28% aqueous sodium hydroxide solution from 207 parts to 110 parts). The water retention value of the carrier (C19) was 4 g/g. The carrier (C19) contained 0.1 mg/g of the artificial polypeptide (P1).

Example 20

A crosslinked polyacrylic acid salt particle (A8) and a carrier for cell culture (C20) were obtained in the same manner as Example 1 except for (changing the used amount of the crosslinkable monomer {ethylene glycol diglycidyl ether} from 4.52 parts to 6.91 parts). The water retention value of the carrier (C20) was 7 g/g. The carrier (C20) contained 0.5 mg/g of artificial polypeptide (P1).

Example 21

A crosslinked polyacrylic acid salt particle (A9) and a carrier for cell culture (C21) were obtained in the same manner as Example 1 except for (changing the used amount of the crosslinkable monomer {ethylene glycol diglycidyl ether} from 4.52 parts to 0.0166 part). The water retention value of the carrier (C21) was 28 g/g. The carrier (C21) contained 8 mg/g of the artificial polypeptide (P1).

Example 22

A crosslinked polyacrylic acid salt particle (A10) and a carrier for cell culture (C22) were obtained in the same manner as Example 1 except for (changing the used amount of the crosslinkable monomer {ethylene glycol diglycidyl ether} from 4.52 parts to 0.0111 part) and (changing the used amount of the methanol/ion exchange water solution containing ethylene glycol diglycidyl ether at solution concentration of 2% from 7.5 to 2.5). The water retention value of the carrier (C22) was 39 g/g. The carrier (C22) contained 10 mg/g of the artificial polypeptide (P1).

Example 23

Preparation of Crosslinked Polyacrylic Acid Salt Particle (A11)

A crosslinked polyacrylic acid salt particle (A11) was obtained in the same manner as Example 1 except for (changing the used amount of the crosslinkable monomer {ethylene glycol diglycidyl ether} from 4.52 parts to 0.0111 part) and (failing to perform surface crosslinking {failing to add the methanol/ion exchange water solution containing ethylene glycol diglycidyl ether at solution concentration of 2% and failing to hold at 80° C. for one hour}).

Preparation of Carrier for Cell Culture (C23)

A carrier for cell culture (C23) was obtained in the same manner as Example 1 except for (using the crosslinked polyacrylic acid salt particle (A11) instead of the crosslinked polyacrylic acid salt particle (A1)). The water retention value of the carrier (C23) was 48 g/g. The carrier (C23) contained 12 mg/g of the artificial polypeptide (P1).

Example 24

A crosslinked polyacrylic acid salt particle (A12) and a carrier for cell culture (C24) were obtained in the same manner as Example 18 except for (using 207 parts of an 80% aqueous methacrylic acid solution instead of 173 parts of the 80% aqueous acrylic acid solution). The water retention value of the carrier (C24) was 20 g/g. The carrier (C24) contained 4 mg/g of the artificial polypeptide (P1).

Example 25

A carrier for cell culture (C25) was prepared in the same manner as Example 1 except for (using an artificial polypeptide (P14) {a polypeptide "ProNectin L" having an Mw of about 110,000 which was prepared in accordance with the method described in an Example in JP 3-502935 T and which had a structure where 13 Ile Lys Val Ala Val sequences (7) (x2) and 12 (Gly Ala Gly Ala Gly Ser)9 sequences (21) (y1) were chemically bonded alternately) instead of the artificial polypeptide (P1)). The water retention value of the carrier (C25) was 13 g/g. The carrier (C25) contained 1 mg/g of the artificial polypeptide (P14).

Example 26

A crosslinked polyacrylic acid salt particle (A2) and a carrier for cell culture (C26) were prepared in the same manner as Example 1 except for (changing the used amount of the crosslinkable monomer, ethylene glycol diglycidyl ether, in the polymerization from 4.52 parts to 1.81 parts) and (using the artificial polypeptide (P14) instead of the artificial polypeptide (P1)). The water retention value of the carrier (C26) was 18 g/g. The carrier (C26) contained 3 mg/g of the artificial polypeptide (P14).

Example 27

A crosslinked polyacrylic acid salt particle (A3) and a carrier for cell culture (C27) were prepared in the same manner as Example 1 except for (changing the used amount of the crosslinkable monomer, ethylene glycol diglycidyl ether, in the polymerization from 4.52 parts to 0.90 part) and (using the artificial polypeptide (P14) instead of the artificial polypeptide (P1)). The water retention value of the carrier (C27) was 21 g/g. The carrier (C27) contained 5 mg/g of the artificial polypeptide (P14).

Example 28

A crosslinked polyacrylic acid salt particle (A4) and a carrier for cell culture (C28) were prepared in the same manner as Example 1 except for (changing the used amount of the crosslinkable monomer, ethylene glycol diglycidyl ether, in the polymerization from 4.52 parts to 0.09 part) and (using the artificial polypeptide (P14) instead of the artificial polypeptide (P1)). The water retention value of the carrier (C28) was 23 g/g. The carrier (C28) contained 5 mg/g of the artificial polypeptide (P14).

Example 29

A crosslinked polyacrylic acid salt particle (A3) and a carrier for cell culture (C29) were prepared in the same manner as Example 1 except for (changing the used amount of the crosslinkable monomer, ethylene glycol diglycidyl ether, in the polymerization from 4.52 parts to 0.90 part) and (using an artificial polypeptide (P15) {a polypeptide "ProNectin L2" having an Mw of about 20,000 which was prepared in accordance with the method described in an Example in JP 3-502935 T and which had a structure where five Ile Lys Val Ala Val sequences (7) (x2) and five (Gly Ala Gly Ala Gly Ser)$_9$ sequences (21) (y2) were chemically bonded alternately) instead of the artificial polypeptide (P1)). The water retention value of the carrier (C29) was 21 g/g. The carrier (C29) contained 1 mg/g of the artificial polypeptide (P15).

Example 30

A crosslinked polyacrylic acid salt particle (A3) and a carrier for cell culture (C30) were prepared in the same manner as Example 1 except for (changing the used amount of the crosslinkable monomer, ethylene glycol diglycidyl ether, in the polymerization from 4.52 parts to 0.90 part) and (using an artificial polypeptide (P16) {a polypeptide "ProNectin L3" having an Mw of about 10,000 which was prepared in accordance with the method described in an Example in JP 3-502935 T and which had a structure where three Ile Lys Val Ala Val sequences (7) (x2) and three (Gly Ala Gly Ala Gly Ser)$_9$ sequences (21) (y2) were chemically bonded alternately) instead of the artificial polypeptide (P1)). The water retention value of the carrier (C30) was 21 g/g. The carrier (C30) contained 1 mg/g of the artificial polypeptide (P16).

Example 31

A crosslinked polyacrylic acid salt particle (A3) and a carrier for cell culture (C31) were prepared in the same manner as Example 1 except for (changing the used amount of the crosslinkable monomer, ethylene glycol diglycidyl ether, in the polymerization from 4.52 parts to 0.90 part) and (using an artificial polypeptide (P17) {a polypeptide having an Mw of 529 which had an Ile Lys Val Ala Val sequence (x2); Ile Lys Val Ala Val sequence (7), produced by NeoSystem Co., Ltd.} instead of the artificial polypeptide (P1)). The water retention value of the carrier (C31) was 21 g/g. The content of the artificial polypeptide (P17) of the carrier (C31) was 0.1 mg/g.

Example 32

A crosslinked polyacrylic acid salt particle (A5) and a carrier for cell culture (C32) were prepared in the same manner as Example 1 except for (changing the used amount of the crosslinkable monomer, ethylene glycol diglycidyl ether, in the polymerization from 4.52 parts to 0.90 part) and (using the artificial polypeptide (P14) instead of the artificial polypeptide (P1)). The water retention value of the carrier (C32) was 22 g/g. The carrier (C32) contained 6 mg/g of the artificial polypeptide (P14).

Example 33

Preparation of Artificial Polypeptide (P18)

An artificial polypeptide (P18) {a polypeptide having about 10 Ila Lys Val Ala Val sequences (7)} was obtained in the same manner as "Preparation of artificial polypeptide (P5)" in Example 9 except for (using the artificial polypeptide (P17) instead of the artificial polypeptide (P1)).

Preparation of Carrier for Cell Culture (C33)

A crosslinked polyacrylic acid salt particle (A3) and a carrier for cell culture (C33) were prepared in the same manner as Example 1 except for (changing the used amount of the crosslinkable monomer, ethylene glycol diglycidyl ether, in the polymerization from 4.52 parts to 0.90 part) and (using the artificial polypeptide (P18) instead of the artificial polypeptide (P1)). The water retention value of the carrier (C33) was 21 g/g. The carrier (C33) contained 0.3 mg/g of artificial polypeptide (P18).

Example 34

Preparation of Artificial Polypeptide (P19)

An artificial polypeptide (P19) {having about 20 Ile Lys Val Ala Val sequences (7)} was obtained in the same manner as Example 9(1) except for (using the artificial polypeptide (P18) instead of using the artificial polypeptide (P4)), (using trade name: Superdex 75 pg as a gel filtration column instead of using trade name: Superdex 30 pg), and (separating a fraction with an Mw of about 10,000 instead of the fraction with an Mw of about 1,000).

Preparation of Carrier for Cell Culture (C34)

A crosslinked polyacrylic acid salt particle (A3) and a carrier for cell culture (C34) were prepared in the same manner as Example 1 except for (changing the used amount of the crosslinkable monomer, ethylene glycol diglycidyl ether, in the polymerization from 4.52 parts to 0.90 part) and (using the artificial polypeptide (P19) instead of the artificial polypeptide (P1)). The water retention value of the carrier (C34) was 21 g/g. The carrier (C34) contained 0.7 mg/g of the artificial polypeptide (P19).

Example 35

Preparation of Artificial Polypeptide (P20)

An artificial polypeptide (P20) {having about 30 Ile Lys Val Ala Val sequences (7)} was obtained in the same manner as Example 9(1) except for (causing the artificial polypeptide (P18) and the artificial polypeptide (P19) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 15,000 instead of the fraction with an Mw of about 1,000).

Preparation of Carrier for Cell Culture (C35)

A crosslinked polyacrylic acid salt particle (A3) and a carrier for cell culture (C35) were prepared in the same manner as Example 1 except for (changing the used amount of the crosslinkable monomer, ethylene glycol diglycidyl ether, in the polymerization from 4.52 parts to 0.90 part) and (using the artificial polypeptide (P20) instead of the artificial polypeptide (P1)). The water retention value of the carrier (C35) was 21 g/g. The carrier (C35) contained 1 mg/g of the artificial polypeptide (P20).

Example 36

Preparation of Artificial Polypeptide (P21)

An artificial polypeptide (P21) {having about 40 Ile Lys Val Ala Val sequences (7)} was prepared in the same manner as Example 9(1) except for (causing the artificial polypeptides (P19) themselves to react instead of causing the artificial polypeptides (P4) themselves to react), (using trade name: Superdex 75 pg as a gel filtration column instead of using trade name: Superdex 30 pg), and (separating a fraction with an Mw of about 20,000 instead of the fraction with an Mw of about 1,000).

Preparation of Carrier for Cell Culture (C36)

A crosslinked polyacrylic acid salt particle (A3) and a carrier for cell culture (C36) were prepared in the same manner as Example 1 except for (changing the used amount of the crosslinkable monomer, ethylene glycol diglycidyl ether, in the polymerization from 4.52 parts to 0.90 part) and (using the artificial polypeptide (P21) instead of the artificial polypeptide (P1)). The water retention value of the carrier (C36) was 21 g/g. The carrier (C36) contained 2 mg/g of the artificial polypeptide (P21).

Example 37

Preparation of Artificial Polypeptide (P22)

An artificial polypeptide (P22) {having about one Ile Lys Val Ala Val sequence (7) and about one Gly Ala Gly Ala Gly Ser sequence (64)} was prepared in the same manner as Example 9(1) except for (causing the artificial polypeptide (P17) and a polypeptide composed of Gly Ala Gly Ala Gly Ser sequence (64) to react at a molar ratio of 1:1 instead of causing the artificial polypeptides (P4) themselves to react).

Preparation of Carrier for Cell Culture (C37)

A crosslinked polyacrylic acid salt particle (A3) and a carrier for cell culture (C37) were prepared in the same manner as Example 1 except for (changing the used amount of the crosslinkable monomer, ethylene glycol diglycidyl ether, in the polymerization from 4.52 parts to 0.90 part) and (using the artificial polypeptide (P22) instead of the artificial polypeptide (P1)). The water retention value of the carrier (C37) was 21 g/g. The carrier (C37) contained 0.2 mg/g of artificial polypeptide (P22).

Example 38

Preparation of Artificial Polypeptide (P23)

An artificial polypeptide (P23) {having about one Ile Lys Val Ala Val sequence (7) and about 10 Gly Ala Gly Ala Gly Ser sequences (64)} was prepared in the same manner as Example 9(1) except for (causing the artificial polypeptide (P17) and the artificial polypeptide (P10D) to react at a molar ratio of 1:1 instead of causing the artificial polypeptides (P4) themselves to react), and (separating a fraction with an Mw of about 5,000 instead of the fraction with an Mw of about 1,000).

Preparation of Carrier for Cell Culture (C38)

A crosslinked polyacrylic acid salt particle (A3) and a carrier for cell culture (C38) were prepared in the same manner as Example 1 except for (changing the used amount of the crosslinkable monomer, ethylene glycol diglycidyl ether, in the polymerization from 4.52 parts to 0.90 part) and (using the artificial polypeptide (P23) instead of the artificial polypeptide (P1)). The water retention value of the carrier (C38) was 21 g/g. The carrier (C38) contained 0.5 mg/g of the artificial polypeptide (P23).

Example 39

Preparation of Artificial Polypeptide (P24)

An artificial polypeptide (P24) {having about one Ile Lys Val Ala Val sequence (7) and about 20 Gly Ala Gly Ala Gly Ser sequences (64)} was prepared in the same manner as Example 9(1) except for (causing the artificial polypeptide (P17) and the artificial polypeptide (P11A) to react at a molar ratio of 1:1 instead of causing the artificial polypeptides (P4) themselves to react), and (separating a fraction with an Mw of about 9,000 instead of the fraction with an Mw of about 1,000).

Preparation of Carrier for Cell Culture (C39)

A crosslinked polyacrylic acid salt particle (A3) and a carrier for cell culture (C39) were prepared in the same manner as Example 1 except for (changing the used amount of the crosslinkable monomer, ethylene glycol diglycidyl ether, in the polymerization from 4.52 parts to 0.90 part) and (using the artificial polypeptide (P24) instead of the artificial polypeptide (P1)). The water retention value of the carrier (C39) was 21 g/g. The carrier (C39) contained 1 mg/g of the artificial polypeptide (P24).

Example 40

Preparation of Artificial Polypeptide (P25)

An artificial polypeptide (P25) {having about one Ile Lys Val Ala Val sequence (7) and about 30 Gly Ala Gly Ala Gly Ser sequences (64)} was obtained in the same manner as Example 9(1) except for (causing the artificial polypeptide (P17) and the artificial polypeptide (P12A) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 13,000 instead of the fraction with an Mw of about 1,000).

Preparation of Carrier for Cell Culture (C40)

A crosslinked polyacrylic acid salt particle (A3) and a carrier for cell culture (C40) were prepared in the same manner as Example 1 except for (changing the used amount of the crosslinkable monomer, ethylene glycol diglycidyl ether, in the polymerization from 4.52 parts to 0.90 part) and (using the artificial polypeptide (P25) instead of the artificial polypep-

Example 41

Preparation of Artificial Polypeptide (P26)

An artificial polypeptide (P26) {having about one Ile Lys Val Ala Val sequence (7) and about 50 Gly Ala Gly Ala Gly Ser sequences (64)} was obtained in the same manner as Example 9(1) except for (causing the artificial polypeptide (P17) and the artificial polypeptide (P13A) to react at a molar ratio of 1:1 instead of causing the artificial polypeptides (P4) themselves to react), (using trade name: Superdex 75 pg as a gel filtration column instead of using trade name: Superdex 30 pg), and (separating a fraction with an Mw of about 21,000 instead of the fraction with an Mw of about 1,000).

Preparation of Carrier for Cell Culture (C41)

A crosslinked polyacrylic acid salt particle (A3) and a carrier for cell culture (C41) were prepared in the same manner as Example 1 except for (changing the used amount of the crosslinkable monomer, ethylene glycol diglycidyl ether, in the polymerization from 4.52 parts to 0.90 part) and (using the artificial polypeptide (P26) instead of the artificial polypeptide (P1)). The water retention value of the carrier (C41) was 21 g/g. The carrier (C41) contained 2 mg/g of the artificial polypeptide (P26).

Example 42

A carrier for cell culture (C42) was prepared in the same manner as Example 1 except for (using the crosslinked polyacrylic acid salt particle (A6) instead of the crosslinked polyacrylic acid salt particle (A1)) and (using the artificial polypeptide (P14) instead of the artificial polypeptide (P1)). The water retention value of the carrier (C42) was 21 g/g. The carrier (C42) contained 8 mg/g of the artificial polypeptide (P14).

Example 43

A carrier for cell culture (C43) was prepared in the same manner as Example 1 except for (using the crosslinked polyacrylic acid salt particle (A7) {Example 19} instead of the crosslinked polyacrylic acid salt particle (A1)) and (using the artificial polypeptide (P14) instead of the artificial polypeptide (P1)). The water retention value of the carrier (C43) was 4 g/g. The carrier (C43) contained 0.1 mg/g of the artificial polypeptide (P14).

Example 44

A carrier for cell culture (C44) was prepared in the same manner as Example 1 except for (using the crosslinked polyacrylic acid salt particle (A8) {Example 20} instead of the crosslinked polyacrylic acid salt particle (A1)) and (using the artificial polypeptide (P14) instead of the artificial polypeptide (P1)). The water retention value of the carrier (C44) was 7 g/g. The carrier (C44) contained 0.2 mg/g of the artificial polypeptide (P14).

Example 45

A carrier for cell culture (C45) was prepared in the same manner as Example 1 except for (using the crosslinked polyacrylic acid salt particle (A9) {Example 21} instead of the crosslinked polyacrylic acid salt particle (A1)) and (using the artificial polypeptide (P14) instead of the artificial polypeptide (P1)). The water retention value of the carrier (C45) was 28 g/g. The carrier (C45) contained 6 mg/g of the artificial polypeptide (P14).

Example 46

A carrier for cell culture (C46) was prepared in the same manner as Example 1 except for (using the crosslinked polyacrylic acid salt particle (A10) {Example 22} instead of the crosslinked polyacrylic acid salt particle (A1)) and (using the artificial polypeptide (P14) instead of the artificial polypeptide (P1)). The water retention value of the carrier (C46) was 39 g/g. The carrier (C46) contained 10 mg/g of the artificial polypeptide (P14).

Example 47

A carrier for cell culture (C47) was prepared in the same manner as Example 1 except for (using the crosslinked polyacrylic acid salt particle (A11) {Example 23} instead of the crosslinked polyacrylic acid salt particle (A1)) and (using the artificial polypeptide (P14) instead of the artificial polypeptide (P1)). The water retention value of the carrier (C47) was 48 g/g. The carrier (C47) contained 10 mg/g of the artificial polypeptide (P14).

Example 48

A carrier for cell culture (C48) was prepared in the same manner as Example 1 except for (using the crosslinked polyacrylic acid salt particle (A12) {Example 24} instead of the crosslinked polyacrylic acid salt particle (A1)) and (using the artificial polypeptide (P14) instead of the artificial polypeptide (P1)). The water retention value of the carrier (C48) was 20 g/g. The carrier (C48) contained 2 mg/g of the artificial polypeptide (P14).

Example 49

A spray liquid (1) was obtained by dissolving a water-soluble carbodiimide {1-ethyl-3-(3-dimethylaminopropyl) carbodiimide hydrochloride, produced by Dojindo Laboratories} in PBS at concentration of 0.1 mM. A spray liquid (2) was obtained by dissolving the artificial polypeptide (P1) in PBS at concentration of 1 μg/mL.

While 0.4 mL of the spray liquid (1) was sprayed to 1 g of the crosslinked polyacrylic acid salt particle (A3), mixing and stirring was performed using a spatula at about 25° C. for 2 minutes. Then, a reaction was allowed to occur while leaving at rest for one hour to obtain a carbodiimide bond particle.

Subsequently, while 0.4 mL of the spray liquid (2) was sprayed to the carbodiimide bonded particle, a reaction was allowed to occur for one hour by mixing and stirring at about 25° C. to obtain an artificial polypeptide bonded particle. Then, a washing operation composed of addition of 40 mL of PBS to the artificial polypeptide bonded particle and suction removal thereof was repeated five times. Moreover, a washing operation composed of addition of 40 mL of ion exchange water and suction removal thereof was repeated twice.

Finally, the resultant was placed in a vacuum dryer, and was subjected to drying at 120° C., 0.1 kPa or less for 4 hours to yield a carrier for cell culture (C49) of the present invention. The water retention value of the carrier (C49) was 21 g/g. The carrier (C49) contained 5 ng/g of the artificial polypeptide (P1).

Example 50

A carrier for cell culture (C50) of the present invention was obtained in the same manner as Example 49 except for (changing the concentration of the water-soluble carbodiimide from 0.1 mM to 0.5 mM) and (changing the concentration of the artificial polypeptide (P1) from 1 μg/mL to 5 μg/mL). The water retention value of the carrier (C50) was 21 g/g. The carrier (C50) contained 50 ng/g of the artificial polypeptide (P1).

Example 51

A carrier for cell culture (C51) of the present invention was obtained in the same manner as Example 49 except for (changing the concentration of the water-soluble carbodiimide from 0.1 mM to 2 mM) and (changing the concentration of the artificial polypeptide (P1) from 1 μg/mL to 20 μg/mL). The water retention value of the carrier (C51) was 21 g/g. The carrier (C51) contained 500 ng/g of the artificial polypeptide (P1).

Example 52

A carrier for cell culture (C52) of the present invention was obtained in the same manner as Example 1 except for (using the crosslinked polyacrylic acid salt particle (A3) instead of the crosslinked polyacrylic acid salt particle (A1)), (changing the concentration of the water-soluble carbodiimide from 60 mM to 500 mM), and (changing the concentration of the artificial polypeptide (P1) from 600 μg/mL to 5 mg/mL). The water retention value of the carrier (C52) was 19 g/g. The carrier (C52) contained 50 mg/g of the artificial polypeptide (P1).

Example 53

A carrier for cell culture (C53) of the present invention was obtained in the same manner as Example 1 except for (using the crosslinked polyacrylic acid salt particle (A3) instead of the crosslinked polyacrylic acid salt particle (A1)), (changing the concentration of the water-soluble carbodiimide from 60 mM to 500 mM), and (changing the concentration of the artificial polypeptide (P1) from 600 μg/mL to 25 mg/mL). The water retention value of the carrier (C53) was 14 g/g. The carrier (C53) contained 500 mg/g of the artificial polypeptide (P1).

Comparative Example 1

The crosslinked polyacrylic acid salt particle (A3) was used as a carrier for cell culture for comparison purpose (C54). The water retention value of the carrier (C54) was 21 g/g.

Comparative Example 2

A commercially available collagen bonded dextran bead (trade name: Cytodex 3, produced by Amersham Biosciences Corporation (General Electronic Company)) was used as a carrier for cell culture (C55) for comparison purpose. The water retention value of the carrier (C55) was 9 g/g.

Comparative Example 3

A carrier for cell culture (C56) for comparison purpose was obtained as follows with reference to the description of Example 1 of JP 2003-189848 A. Polystyrene beads obtained by suspension polymerization of 99% of styrene and 1% of divinylbenzene were classified with a 63 μm sieve and a 53 μm sieve (JIS Z8801-1:2000) to obtain particles having a particle diameter from 53 to 63 μm.

Subsequently, a 4.5 N aqueous lithium perchlorate solution containing the artificial polypeptide (P1) {concentration of artificial polypeptide (P1): 1 mg/mL} was diluted with a phosphoric acid buffer liquid (PBS) so that the concentration of the artificial polypeptide (P1) might become 15 μg/mL, thereby preparing an artificial polypeptide (P1) solution.

To 25 mL of a solution of the artificial polypeptide (P1), 5 g of the beads obtained above were added and stirred for 12 hours with a stirrer made of polyfluoroethylene resin {Teflon (registered trademark)}. The resulting bead slurry was transferred to a stainless vat mounted on a shaker and then it was shaken and dried for 24 hours under blowing hot air of 100° C. The resulting dry beads were washed with 50 mL of PBS twice, and then dried to obtain a carrier for cell culture (C56) for comparison purpose. The water retention value of the carrier (C56) was 0 g/g. The carrier (C56) contained 1 mg/g of the artificial polypeptide (P1).

Comparative Example 4

Into a reaction vessel equipped with a stirrer, a monomer feeding tube, a nitrogen gas introducing tube, a thermometer, and a reflux condenser, 624 parts of cyclohexane and 3.1 parts of sorbitan monostearate as a polymerization dispersing agent were charged, and then nitrogen bubbling was performed for 30 minutes or more to expel the dissolved air, followed by raising the temperature to 75° C. Into another reactor, 138 parts of acrylamide and 242 parts of water were charged. To the resulting aqueous solution, 0.0098 part of a crosslinkable monomer (N,N'-methylenebisacrylamide), 0.278 part a polymerization initiator (potassium persulfate) and 0.053 part of a chain transfer agent (sodium hypophosphite) were added, and then nitrogen bubbling was performed to expel the dissolved air, thereby obtaining an aqueous monomer solution.

The resulting aqueous monomer solution was fed into the cyclohexane solution under stirring (the stirring speed was 500 rpm) in the polymerization reaction vessel through the monomer feeding tube of the polymerization reaction vessel, continuously at a rate of 6.5 mL/min over about one hour, and polymerization was performed under cyclohexane reflux. Subsequently, after removal of 160 parts of water by azeotropic dehydration, a water-containing gel polymer was taken out, followed by drying at 120° C. for 2 hours to obtain dry crosslinked polyacrylamide. The dry crosslinked polyacrylamide was classified with a 63 μm sieve and a 53 μm sieve (JIS Z8801-1:2000) to obtain particles {crosslinked polyacrylamide particles} having a particle diameter from 53 to 63 μm.

A carrier for cell culture (C57) for comparison purpose was obtained in the same manner as Example 1 except for (using the crosslinked polyacrylamide particles instead of the crosslinked polyacrylic acid salt particle (A1)). The water retention value of the carrier (C57) was 4 g/g. The carrier (C57) contained 0.1 mg/g of artificial polypeptide (P1).

Comparative Example 5

A carrier for cell culture (C58) for comparison purpose was obtained in the same manner as Comparative Example 3 except for (using the artificial polypeptide (P14) instead of the artificial polypeptide (P1)). The water retention value of the carrier (C58) was 0 g/g. The carrier (C58) contained 1 mg/g of the artificial polypeptide (P14).

Comparative Example 6

A carrier for cell culture (C59) for comparison purpose was prepared in the same manner as Comparative Example 4 except for (using the artificial polypeptide (P14) instead of the artificial polypeptide (P1)). The water retention value of the carrier (C59) was 4 g/g. The carrier (C59) contained 0.1 mg/g of the artificial polypeptide (P14).

Cell Proliferativity Evaluation 1

As to the carriers for cell culture (C1)-(C24) and (C49)-(C57) of Examples 1-24, 49-53 and Comparative Examples 1-4, each carrier was charged into a spinner flask having operation volume of 100 mL so that a matter resulting from removal of excess water from a carrier for cell culture swollen with physiological saline by subjecting the carrier to centrifugal dehydration for 90 seconds at 150G might have come to weigh 4 g. That is, 0.29 g of carrier (C1), 0.21 g of carrier (C2), 0.18 g of carrier (C3), 0.17 g of carrier (C4), 0.18 g of carriers (C5)-(C7), 0.17 g of carrier (C8), 0.18 g of carriers (C9)-(C17), 0.18 g of carrier (C18), 0.80 g of carrier (C19), 0.50 g of carrier (C20), 0.14 g of carrier (C21), 0.10 g of carrier (C22), 0.08 g of carrier (C23), 0.19 g of carrier (C24), 0.18 g of carriers (C49)-(C51), 0.20 g of carrier (C52), 0.27 g of carrier (C53), 0.18 g of carrier (C54), 0.40 g of carrier (C55), 4 g of carrier (C56), and 0.80 g of carrier (C57) were each charged into the spinner flask.

Then, to each spinner flask, 100 mL/flask of physiological saline was added, followed by autoclave sterilization (at 121° C., for 20 minutes). After the autoclave sterilization, the physiological saline was removed by suction with an aspirator, and then a serum-free medium which was obtained by causing a serum-free medium (trade name: VP-SFM, produced by Invitrogen Corporation) to contain 0.2% by weight of an antimicrobial agent (trade name: PSA, produced by Cascade) was added in an amount of 50 mL/flask, followed by being left at rest for one hour. Then, the medium was removed by suction and subsequently the same type of the serum-free medium was added again in an amount of 100 mL/flask. The spinner flask was left at rest for two hours in a $CO_2$ incubator conditioned at 37° C. and carbon dioxide gas concentration of 5 vol %, and then VERO cells (produced by Dainippon Sumitomo Pharma Co., Ltd.), which had been preliminarily cultured, were seeded on the serum-free medium so that the cell concentration might become 200,000 cells/mL. Culture was performed for seven days under stirring at 30 rpm in a $CO_2$ incubator conditioned at 37° C. and carbon dioxide gas concentration of 5 von. Here, every half of the medium was exchanged on the fourth day, the fifth day, and the sixth day. On the seventh day of the culture, a sample was taken and the cell concentration ($\times 10^4$ cells/mL) in the medium was determined by counting the number of cell nuclei per unit volume by the cell nuclei-counting method using crystal violet. The results were shown in Table 1 with the water retention values of the carriers for cell culture.

TABLE 1

| | | Artificial polypeptide (P) | | | |
|---|---|---|---|---|---|
| | | The number of sequence (s) (X) | The number of sequence (s) (Y) | Water retention value (g/g) | Cell concentration ($\times 10^4$ cells/mL) |
| Example | 1 | 13 | 12 | 13 | 88 |
| | 2 | 13 | 12 | 18 | 113 |
| | 3 | 13 | 12 | 21 | 146 |
| | 4 | 13 | 12 | 23 | 61 |
| | 5 | 5 | 5 | 21 | 130 |
| | 6 | 3 | 3 | 21 | 77 |
| | 7 | 1 | 0 | 21 | 30 |
| | 8 | 13 | 12 | 22 | 107 |
| | 9 | 10 | 0 | 21 | 43 |
| | 10 | 20 | 0 | 21 | 36 |
| | 11 | 30 | 0 | 21 | 26 |
| | 12 | 40 | 0 | 21 | 26 |
| | 13 | 1 | 1 | 21 | 40 |
| | 14 | 1 | 10 | 21 | 41 |
| | 15 | 1 | 20 | 21 | 31 |
| | 16 | 1 | 30 | 21 | 25 |
| | 17 | 1 | 50 | 21 | 23 |
| | 18 | 13 | 12 | 21 | 82 |
| | 19 | 13 | 12 | 4 | 29 |
| | 20 | 13 | 12 | 7 | 29 |
| | 21 | 13 | 12 | 28 | 60 |
| | 22 | 13 | 12 | 39 | 29 |
| | 23 | 13 | 12 | 48 | 28 |
| | 24 | 13 | 12 | 20 | 94 |
| | 49 | 13 | 12 | 21 | 20 |
| | 50 | 13 | 12 | 21 | 32 |
| | 51 | 13 | 12 | 21 | 87 |
| | 52 | 13 | 12 | 19 | 54 |
| | 53 | 13 | 12 | 14 | 25 |
| Comparative Example | 1 | — | — | 21 | 6 |
| | 2 | — | — | 9 | 15 |
| | 3 | 13 | 12 | 0 | 14 |
| | 4 | 13 | 12 | 4 | 10 |

The results in Table 1 clearly showed that while VERO cells did not proliferate at all in the carrier for cell culture of Comparative Examples 1-4, VERO cells proliferated well in the carriers for cell culture of the present invention (Examples 1-24 and 49-53).

Cell Proliferativity Evaluation 2

The cell concentration ($\times 10^4$ cells/mL) in a medium was determined in the same manner as <Cell proliferativity evaluation 1> except for (changing the serum-free medium (trade name: VP-SFM, produced by Invitrogen Corporation) to a serum-free medium (trade name: Opti-PRO™ SFM, produced by Invitrogen Corporation)) and (changing the VERO cells to MDCK cells (produced by Dainippon Sumitomo Pharma Co., Ltd.)). The results were shown in Table 2 with the water retention values of the carriers for cell culture.

TABLE 2

| | | Artificial polypeptide (P) | | | |
|---|---|---|---|---|---|
| | | The number of sequence (s) (X) | The number of sequence (s) (Y) | Water retention value (g/g) | Cell concentration ($\times 10^4$ cells/mL) |
| Example | 1 | 13 | 12 | 13 | 158 |
| | 2 | 13 | 12 | 18 | 180 |
| | 3 | 13 | 12 | 21 | 227 |
| | 4 | 13 | 12 | 23 | 182 |
| | 5 | 5 | 5 | 21 | 220 |
| | 6 | 3 | 3 | 21 | 189 |
| | 7 | 1 | 0 | 21 | 111 |
| | 8 | 13 | 12 | 22 | 207 |
| | 9 | 10 | 0 | 21 | 121 |

TABLE 2-continued

| | | Artificial polypeptide (P) | | |
|---|---|---|---|---|
| | The number of sequence (s) (X) | The number of sequence (s) (Y) | Water retention value (g/g) | Cell concentration (×10$^4$ cells/mL) |
| 10 | 20 | 0 | 21 | 105 |
| 11 | 30 | 0 | 21 | 90 |
| 12 | 40 | 0 | 21 | 83 |
| 13 | 1 | 1 | 21 | 128 |
| 14 | 1 | 10 | 21 | 128 |
| 15 | 1 | 20 | 21 | 120 |
| 16 | 1 | 30 | 21 | 90 |
| 17 | 1 | 50 | 21 | 60 |
| 18 | 13 | 12 | 21 | 154 |
| 19 | 13 | 12 | 4 | 68 |
| 20 | 13 | 12 | 7 | 63 |
| 21 | 13 | 12 | 28 | 108 |
| 22 | 13 | 12 | 39 | 74 |
| 23 | 13 | 12 | 48 | 66 |
| 24 | 13 | 12 | 20 | 158 |
| 49 | 13 | 12 | 21 | 45 |
| 50 | 13 | 12 | 21 | 49 |
| 51 | 13 | 12 | 21 | 131 |
| 52 | 13 | 12 | 19 | 81 |
| 53 | 13 | 12 | 14 | 46 |
| Comparative Example 1 | — | — | 21 | 12 |
| 2 | — | — | 9 | 39 |
| 3 | 13 | 12 | 0 | 37 |
| 4 | 13 | 12 | 4 | 15 |

The results in Table 2 clearly showed that MDCK cells proliferated remarkably in the carriers for cell culture of the present invention (Examples 1-24 and 49-53) in comparison to the carriers for cell culture of Comparative Examples 1-4.

Cell Proliferativity Evaluation 3

As to the carriers for cell culture (C1)-(C24) and (C49)-(C57) of Examples 1-24, 49-53 and Comparative Examples 1-4, each carrier was charged into a spinner flask having operation volume of 10 mL so that a matter resulting from removal of excess water from a carrier for cell culture swollen with physiological saline by subjecting the carrier to centrifugal dehydration for 90 seconds at 150G might have come to weigh 0.4 g. That is, 0.029 g of carrier (C1), 0.021 g of carrier (C2), 0.018 g of carrier (C3), 0.017 g of carrier (C4), 0.018 g of carriers (C5)-(C7), 0.017 g of carrier (C8), 0.018 g of carriers (C9)-(C17), 0.018 g of carrier (C18), 0.080 g of carrier (C19), 0.050 g of carrier (C20), 0.014 g of carrier (C21), 0.010 g of carrier (C22), 0.008 g of carrier (C23), 0.019 g of carrier (C24), 0.18 g of carriers (C49)-(C51), 0.20 g of carrier (C52), 0.27 g of carrier (C53), 0.018 g of carrier (C54), 0.040 g of carrier (C55), 0.4 g of carrier (C56), and 0.080 g of carrier (C57) were each charged into a spinner flask.

Then, to each spinner flask, 10 mL/flask of physiological saline was added, followed by autoclave sterilization (at 121° C., for 20 minutes). After the autoclave sterilization, the physiological saline was removed by suction with an aspirator, and then a serum medium {a serum medium obtained by causing an Opti-MEM™ I medium (produced by Invitrogen Corporation) to contain 5 μg/mL of bovine insulin (produced by Sigma-Aldrich Japan K.K.), 400 ng/mL of hydrocortisone (produced by Sigma-Aldrich Japan K.K.), 250 ng/mL of isoproterenol (produced by Sigma-Aldrich Japan K.K.), 10 ng/mL of rhEGF (produced by Sigma-Aldrich Japan K.K.), 10 vol % of bovine embryo serum (produced by Invitrogen Corporation), and 0.2% by weight of an antimicrobial agent (trade name: PSA, produced by Cascade)} was added in an amount of 5 mL/flask, followed by being left at rest for one hour. Then, the medium was removed by suction and subsequently the same type of the serum medium was added again in an amount of 10 mL/flask. The spinner flask was left at rest for two hours in a $CO_2$ incubator conditioned at 37° C. and carbon dioxide gas concentration of 5 vol %, and then epithelial cells (trade name: NHEK (F), produced by Kurabo Industries, Ltd.), which had been preliminarily cultured, were seeded on the serum medium so that the cell concentration might become 200,000 cells/mL. Culture was performed for seven days under stirring at 30 rpm in a $CO_2$ incubator conditioned at 37° C. and carbon dioxide gas concentration of 5 von. Here, every half of the medium was exchanged on the fourth day, the fifth day, and the sixth day. On the seventh day of the culture, a sample was taken and the cell concentration (×10$^4$ cells/mL) in the medium was determined by counting the number of cell nuclei per unit volume by the cell nuclei-counting method using crystal violet. The results were shown in Table 3 with the water retention values of the carriers for cell culture.

TABLE 3

| | | Artificial polypeptide (P) | | |
|---|---|---|---|---|
| | | The number of sequence (s) (X) | The number of sequence (s) (Y) | Water retention value (g/g) | Cell concentration (×10$^4$ cells/mL) |
| Example | 1 | 13 | 12 | 13 | 61 |
| | 2 | 13 | 12 | 18 | 65 |
| | 3 | 13 | 12 | 21 | 75 |
| | 4 | 13 | 12 | 23 | 62 |
| | 5 | 5 | 5 | 21 | 66 |
| | 6 | 3 | 3 | 21 | 56 |
| | 7 | 1 | 0 | 21 | 44 |
| | 8 | 13 | 12 | 22 | 67 |
| | 9 | 10 | 0 | 21 | 49 |
| | 10 | 20 | 0 | 21 | 35 |
| | 11 | 30 | 0 | 21 | 29 |
| | 12 | 40 | 0 | 21 | 24 |
| | 13 | 1 | 1 | 21 | 54 |
| | 14 | 1 | 10 | 21 | 54 |
| | 15 | 1 | 20 | 21 | 49 |
| | 16 | 1 | 30 | 21 | 28 |
| | 17 | 1 | 50 | 21 | 24 |
| | 18 | 13 | 12 | 21 | 48 |
| | 19 | 13 | 12 | 4 | 25 |
| | 20 | 13 | 12 | 7 | 25 |
| | 21 | 13 | 12 | 28 | 48 |
| | 22 | 13 | 12 | 39 | 27 |
| | 23 | 13 | 12 | 48 | 22 |
| | 24 | 13 | 12 | 20 | 47 |
| | 49 | 13 | 12 | 21 | 13 |
| | 50 | 13 | 12 | 21 | 24 |
| | 51 | 13 | 12 | 21 | 48 |
| | 52 | 13 | 12 | 19 | 40 |
| | 53 | 13 | 12 | 14 | 15 |
| Comparative Example | 1 | — | — | 21 | 1 |
| | 2 | — | — | 9 | 11 |
| | 3 | 13 | 12 | 0 | 3 |
| | 4 | 13 | 12 | 4 | 6 |

The results in Table 3 clearly showed that though epithelial cells did not proliferate at all in the carrier for cell culture of Comparative Examples 1-4, epithelial cells proliferated well in the carriers for cell culture of the present invention (Examples 1-24 and 49-53).

Cell Proliferativity Evaluation 4

As to the carriers for cell culture (C25)-(C48), (C54)-(C55), and (C58)-(C59) of Examples 25-48, Comparative Examples 1-2 and Comparative Examples 5-6, each carrier was charged into a spinner flask having operation volume of 100 mL so that a matter resulting from removal of excess water from a carrier for cell culture carrier swollen with physiological saline by subjecting the carrier to centrifugal dehydration for 90 seconds at 150G might come to weigh 4 g. That is, 0.29 g of carrier (C25), 0.21 g of carrier (C26), 0.18 g of carrier (C27), 0.17 g of carrier (C28), 0.18 g of carriers (C29)-(C31), 0.17 g of carrier (C32), 0.18 g of carriers (C33)-(C41), 0.18 g of carrier (C42), 0.80 g of carrier (C43), 0.50 of carrier (C44), 0.14 g of carrier (C45), 0.10 g of carrier (C46), 0.08 g of carrier (C47), 0.19 g of carrier (C48), 0.18 g of carrier (C54), 0.40 g of carrier (C55), 4 g of carrier (C58), 0.80 g of carrier (C59) were each charged into a spinner flask. To each spinner flask, 100 mL/flask of physiological saline was added, followed by autoclave sterilization (at 121° C., for 20 minutes). After the autoclave sterilization, the physiological saline was removed by suction with an aspirator, and then PBS was added in an amount of 50 mL/flask, followed by being left at rest for one hour.

Then, the PBS was removed by suction with an aspirator and a serum medium obtained by addition of 1 vol % of bovine embryo serum (produced by Invitrogen Corporation) to an MEM Dulbecco's liquid medium (produced by Dainippon Sumitomo Pharma Co., Ltd.) was added in an amount of 50 mL/flask, followed by being left at rest for one hour. Then, the medium was removed by suction and subsequently the same type of the serum medium was added again in an amount of 100 mL/flask. The spinner flask was left at rest for two hours in a $CO_2$ incubator conditioned at 37° C. and carbon dioxide gas concentration of 5 vol %, and then HT-1080 cells (produced by Dainippon Sumitomo Pharma Co., Ltd.), which had been preliminarily cultured, were seeded on the medium so that the cell concentration might become 200,000 cells/mL. Culture was performed for seven days under stirring at 30 rpm in a $CO_2$ incubator conditioned at 37° C. and carbon dioxide gas concentration of 5 vol %. Here, every half of the medium was exchanged on the fourth day, the fifth day, and the sixth day. On the seventh day of the culture, a sample was taken and the cell concentration (cells/mL) in the medium was determined by counting the number of cell nuclei per unit volume by the cell nuclei-counting method using crystal violet. The results were shown in Table 4 with the water retention values of the carriers for cell culture.

TABLE 4

| | | Artificial polypeptide (P) | | | |
|---|---|---|---|---|---|
| | | The number of sequence (s) (X) | The number of sequence (s) (Y) | Water retention value (g/g) | Cell concentration ($\times 10^4$ cells/mL) |
| Example | 25 | 13 | 12 | 13 | 71 |
| | 26 | 13 | 12 | 18 | 96 |
| | 27 | 13 | 12 | 21 | 89 |
| | 28 | 13 | 12 | 23 | 74 |
| | 29 | 5 | 5 | 21 | 79 |
| | 30 | 3 | 3 | 21 | 74 |
| | 31 | 1 | 0 | 21 | 50 |
| | 32 | 13 | 12 | 22 | 79 |
| | 33 | 10 | 0 | 21 | 59 |
| | 34 | 20 | 0 | 21 | 51 |
| | 35 | 30 | 0 | 21 | 39 |
| | 36 | 40 | 0 | 21 | 31 |
| | 37 | 1 | 1 | 21 | 61 |

TABLE 4-continued

| | | Artificial polypeptide (P) | | | |
|---|---|---|---|---|---|
| | | The number of sequence (s) (X) | The number of sequence (s) (Y) | Water retention value (g/g) | Cell concentration ($\times 10^4$ cells/mL) |
| | 38 | 1 | 10 | 21 | 64 |
| | 39 | 1 | 20 | 21 | 51 |
| | 40 | 1 | 30 | 21 | 33 |
| | 41 | 1 | 50 | 21 | 33 |
| | 42 | 13 | 12 | 21 | 50 |
| | 43 | 13 | 12 | 4 | 23 |
| | 44 | 13 | 12 | 7 | 31 |
| | 45 | 13 | 12 | 28 | 53 |
| | 46 | 13 | 12 | 39 | 27 |
| | 47 | 13 | 12 | 48 | 26 |
| | 48 | 13 | 12 | 20 | 41 |
| Comparative Example | 1 | — | — | 21 | 6 |
| | 2 | — | — | 9 | 4 |
| | 5 | 13 | 12 | 0 | 15 |
| | 6 | 13 | 12 | 4 | 8 |

The results in Table 4 showed that though HT-1080 cells did not proliferate at all in the carriers for cell culture of Comparative Examples 1-2 and Comparative Examples 5-6, HT-1080 cells proliferated well in the carriers for cell culture of the present invention (Examples 25-48).

INDUSTRIAL APPLICABILITY

The carrier for cell culture of the present invention can exhibit excellent cell proliferativity in serum-free culture and is free from risk of contamination of an infectious factor, such as a virus. Therefore, it is very useful for research, useful substance production, therapies, and the like involved with cells.

For research purpose, it can be used for culture of cells for evaluation of cell functions such as differentiation function, culture of cells for substitution of animal experiments (toxicity test, stimulative test, metabolism function test, and the like), culture of cells for introduction of genes or proteins, and the like.

For useful substance production purpose, it can be used for cells for the production of cytokine, thrombolytic agents, blood coagulation factor formulations, vaccines, hormones, antibiotics, antibodies, growth factors, and the like. Among these, it is suitable for culture of cells for the production of vaccines.

For therapy purpose, it can be used for cell culture of tissues such as skin, skull, muscle, skin tissue, bone, cartilage, blood vessel, nerve, tendon, ligament, trichocyst tissue, mucous membrane tissue, periodontal tissue, dentin, bone marrow, retina, serous membrane, gastrointestinal tract and adipo, as well as of organs such as lung, liver, pancreas and kidney.

The invention claimed is:

1. A carrier for cell culture, comprising:
a particle (A) of a crosslinked poly(meth)acrylic acid or a salt thereof; and
an artificial polypeptide (P) having at least one cell-adhesive minimal amino acid sequence (X) selected from the group consisting of an Arg Gly Asp sequence, a Leu Asp Val sequence, a Leu Arg Glu sequence, a His Ala Val sequence, an Arg Glu Asp Val sequence (1), a Tyr Ile Gly Ser Arg sequence (2), a Pro Asp Ser Gly Arg sequence (3), an Arg Tyr Val Val Leu Pro Arg sequence (4), a Leu Gly Thr Ile Pro Gly sequence (5), an Arg Asn Ile Ala Glu Ile Ile Lys Asp Ile sequence (6), an Ile Lys Val Ala Val sequence (7), an Asp Gly Glu Ala sequence (8), a Gly Val Lys Gly Asp Lys Gly Asn Pro Gly Trp Pro Gly Ala Pro sequence (9), a Gly Glu Phe Tyr Phe Asp Leu Arg Leu Lys Gly Asp Lys sequence (10), a Tyr Lys Leu Asn Val Asn Asp Ser sequence (11), an Ala Lys Pro Ser Tyr Pro Pro Thr Tyr Lys sequence (12), an Asn Arg Trp His Ser Ile Tyr Ile Thr Arg Phe Gly sequence (13), a Thr Trp Tyr Lys Ile Ala Phe Gln Arg Asn Arg Lys sequence (14), an Arg Lys Arg Leu Gln Val Gln Leu Ser Ile Arg Thr (15), and a Pro His Ser Arg Asn (16)
wherein the content of the artificial polypeptide (P) is 500 ng/g to 50 mg/g based on dry weight of the carrier for cell culture;
the carrier for cell culture has a water retention value of from 10 to 28 g/g; and the particle (A) and the artificial polypeptide (P) are bonded together.

2. The carrier for cell culture according to claim 1, wherein the carrier for cell culture is spherical in external shape.

3. The carrier for cell culture according to claim 1, wherein the particle (A) is a particle produced by reversed phase suspension polymerization of an aqueous monomer solution containing (meth)acrylic acid and/or an alkali metal salt of (meth)acrylic acid.

4. The carrier for cell culture according to claim 1, wherein the particle (A) is a particle crosslinked with a surface crosslinking agent.

5. The carrier for cell culture according to claim 1, wherein the number of the cell-adhesive minimal amino acid sequences (X) in one molecule of the artificial polypeptide (P) is 1 to 50.

6. The carrier for cell culture according to claim 1, wherein the cell-adhesive minimal amino acid sequence (X) is an Arg Gly Asp sequence.

7. The carrier for cell culture according to claim 1, wherein the artificial polypeptide (P) is an artificial polypeptide having at least one auxiliary amino acid sequence (Y) having Gly and/or Ala.

8. The carrier for cell culture according to claim 7, wherein the number of the auxiliary amino acid sequences (Y) in one molecule of the artificial polypeptide (P) is 4 to 20.

9. The carrier for cell culture according to claim 7, wherein the auxiliary amino acid sequence (Y) is a (Gly Ala Gly Ala Gly Ser)b sequence,
wherein b is an integer from 1 to 33.

10. The carrier for cell culture according to claim 7, wherein the artificial polypeptide (P) has a structure in which the cell-adhesive minimal amino acid sequence (X) and the auxiliary amino acid sequence (Y) are chemically bonded alternately.

11. The carrier for cell culture according to claim 1, wherein the artificial polypeptide (P) is linked to the particle (A) by chemical bonding and/or physical adsorption.

12. A method for producing a useful substance, comprising:
providing a serum-free medium containing the carrier for cell culture according to claim 1; and
culturing cells on the carrier in the medium to produce the substance.

13. The method according to claim 12, wherein the useful substance is cytokine, an thrombolytic agent, a blood coagulation factor product, a vaccine, a hormone, an antibiotic, an antibody or a growth factor.

14. A method for producing a carrier for cell culture, comprising a step of mixing a particle (A) of a crosslinked poly(meth)acrylic acid or a salt thereof with an artificial polypeptide (P) having at least one cell-adhesive minimal amino acid sequence (X) selected from the group consisting of an Arg Gly Asp sequence, a Leu Asp Val sequence, a Leu Arg Glu sequence, a His Ala Val sequence, an Arg Glu Asp Val sequence (1), a Tyr Ile Gly Ser Arg sequence (2), a Pro Asp Ser Gly Arg sequence (3), an Arg Tyr Val Val Leu Pro Arg sequence (4), a Leu Gly Thr Ile Pro Gly sequence (5), an Arg Asn Ile Ala Glu Ile Ile Lys Asp Ile sequence (6), an Ile Lys Val Ala Val sequence (7), an Asp Gly Glu Ala sequence (8), a Gly Val Lys Gly Asp Lys Gly Asn Pro Gly Trp Pro Gly Ala Pro sequence (9), a Gly Glu Phe Tyr Phe Asp Leu Arg Leu Lys Gly Asp Lys sequence (10), a Tyr Lys Leu Asn Val Asn Asp Ser sequence (11), an Ala Lys Pro Ser Tyr Pro Pro Thr Tyr Lys sequence (12), an Asn Arg Trp His Ser Ile Tyr Ile Thr Arg Phe Gly sequence (13), a Thr Trp Tyr Lys Ile Ala Phe Gln Arg Asn Arg Lys sequence (14), an Arg Lys Arg Leu Gln Val Gln Leu Ser Ile Arg Thr (15), and a Pro His Ser Arg Asn (16) in a solvent to obtain the carrier for cell culture,
wherein the content of the artificial polypeptide (P) is 500 ng/g to 50 mg/g based on dry weight of the carrier for cell culture; and
the carrier for cell culture has a water retention value of from 10 to 28 g/g.

* * * * *